(12) United States Patent
Hibner et al.

(10) Patent No.: US 10,028,765 B2
(45) Date of Patent: Jul. 24, 2018

(54) ULTRASONIC SURGICAL INSTRUMENT CLAMP ARM WITH PROXIMAL NODAL PAD

(71) Applicant: Ethicon Endo-Surgery, LLC, Guaynabo, PR (US)

(72) Inventors: John A. Hibner, Mason, OH (US); Tyler N. Brehm, Arcanum, OH (US); Jeffrey D. Messerly, Cincinnati, OH (US); Kevin L. Houser, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 286 days.

(21) Appl. No.: 14/928,375

(22) Filed: Oct. 30, 2015

(65) Prior Publication Data

US 2017/0119425 A1    May 4, 2017

(51) Int. Cl.
*A61B 17/32* (2006.01)
*A61N 7/00* (2006.01)
*A61B 18/00* (2006.01)

(52) U.S. Cl.
CPC ........ *A61B 17/320092* (2013.01); *A61N 7/00* (2013.01); *A61B 2018/0063* (2013.01); *A61B 2018/00345* (2013.01); *A61B 2018/00595* (2013.01); *A61B 2018/00607* (2013.01); *A61B 2018/00619* (2013.01)

(58) Field of Classification Search
CPC .... A61B 17/320068; A61B 17/320092; A61B 2017/320094; A61B 2017/320096; A61B 2017/320098
See application file for complete search history.

(56) References Cited

U.S. PATENT DOCUMENTS

| | | | |
|---|---|---|---|
| 5,322,055 | A | 6/1994 | Davison et al. |
| 5,324,299 | A | 6/1994 | Davison et al. |
| 5,873,873 | A | 2/1999 | Smith et al. |
| 5,980,510 | A | 11/1999 | Tsonton et al. |
| 6,283,981 | B1 | 9/2001 | Beaupre |
| 6,309,400 | B2 | 10/2001 | Beaupre |
| 6,325,811 | B1 | 12/2001 | Messerly |
| 6,423,082 | B1 | 7/2002 | Houser et al. |

(Continued)

OTHER PUBLICATIONS

U.S. Appl. No. 61/410,603, filed Nov. 5, 2010.
International Search Report and Written Opinion dated Jan. 26, 2017 for Application No. PCT/US2016/058667, 10 pgs.

*Primary Examiner* — Ryan J Severson
(74) *Attorney, Agent, or Firm* — Frost Brown Todd LLC

(57) ABSTRACT

An ultrasonic surgical instrument for cutting a tissue of a patient includes an end effector projecting from a shaft assembly, which has an acoustic waveguide configured to acoustically couple with an ultrasonic transducer. The end effector includes an ultrasonic blade, a clamp arm, and a first clamp pad. The clamp arm is coupled with the shaft assembly and is configured to selectively move relative to the ultrasonic blade from an open position and toward an ultrasonic blade to a closed position. The clamp arm further includes an abutment configured to engage a portion of the shaft assembly in the closed position thereby inhibiting further movement of the clamp arm toward the ultrasonic blade. The first clamp pad thus remains offset from the ultrasonic blade to prevent the first clamp pad from direct contact with the ultrasonic blade.

20 Claims, 29 Drawing Sheets

(56) References Cited

U.S. PATENT DOCUMENTS

| | | |
|---|---|---|
| 6,773,444 B2 | 8/2004 | Messerly |
| 6,783,524 B2 | 8/2004 | Anderson et al. |
| 7,544,200 B2 | 6/2009 | Houser |
| 8,057,498 B2 | 11/2011 | Robertson |
| 8,182,501 B2 * | 5/2012 | Houser .................. A61B 17/12 606/169 |
| 8,460,326 B2 * | 6/2013 | Houser .................. A61B 17/12 606/169 |
| 8,461,744 B2 | 6/2013 | Wiener et al. |
| 8,591,536 B2 | 11/2013 | Robertson |
| 8,623,027 B2 | 1/2014 | Price et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,050,125 B2 * | 6/2015 | Boudreaux .... A61B 17/320092 |
| 9,095,367 B2 | 8/2015 | Olson et al. |
| 9,168,055 B2 * | 10/2015 | Houser .................. A61B 17/12 |
| 9,237,900 B2 * | 1/2016 | Boudreaux .......... A61B 17/282 |
| 9,381,058 B2 | 7/2016 | Houser et al. |
| 9,393,037 B2 | 7/2016 | Olson et al. |
| 2005/0192612 A1 * | 9/2005 | Houser .................. A61B 17/12 606/169 |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0116265 A1 | 5/2012 | Houser et al. |
| 2012/0215244 A1 * | 8/2012 | Houser .................. A61B 17/12 606/169 |
| 2013/0090577 A1 * | 4/2013 | Boudreaux .... A61B 17/320092 601/2 |
| 2013/0253558 A1 * | 9/2013 | Houser .................. A61B 17/12 606/169 |
| 2014/0336698 A1 * | 11/2014 | Boudreaux .......... A61B 17/282 606/206 |
| 2015/0080924 A1 | 3/2015 | Stulen et al. |
| 2015/0265309 A1 * | 9/2015 | Boudreaux .... A61B 17/320092 606/169 |
| 2015/0351792 A1 * | 12/2015 | Houser .................. A61B 17/12 606/171 |
| 2016/0242806 A1 * | 8/2016 | Akagane ........ A61B 17/320092 |
| 2017/0105751 A1 * | 4/2017 | Hibner .......... A61B 17/320092 |

\* cited by examiner

ULTRASONIC SURGICAL INSTRUMENT CLAMP ARM WITH PROXIMAL NODAL PAD

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2008/0234710, entitled "Ultrasonic Surgical Instruments," published Sep. 25, 2008, now U.S. Pat. No. 8,911,460, issued Dec. 16, 2014, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," now U.S. Pat. No. 9,393,037, issued Jul. 19, 2016, the disclosure of which is incorporated by reference herein; and U.S. Pub. No. 2014/0114334, published Apr. 24, 2014, entitled "Flexible Harmonic Waveguides/Blades for Surgical Instruments," now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
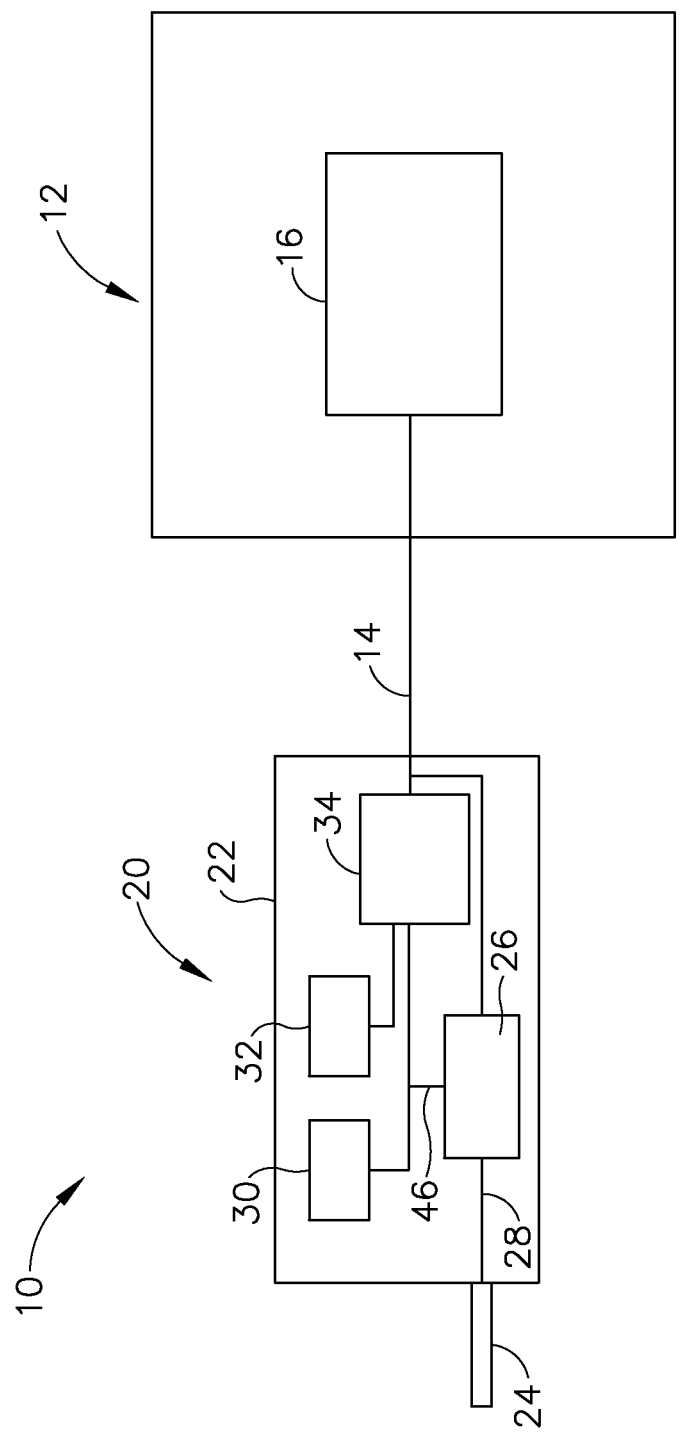
FIG. 1 depicts a block schematic view of an exemplary surgical system.
Figure 2:
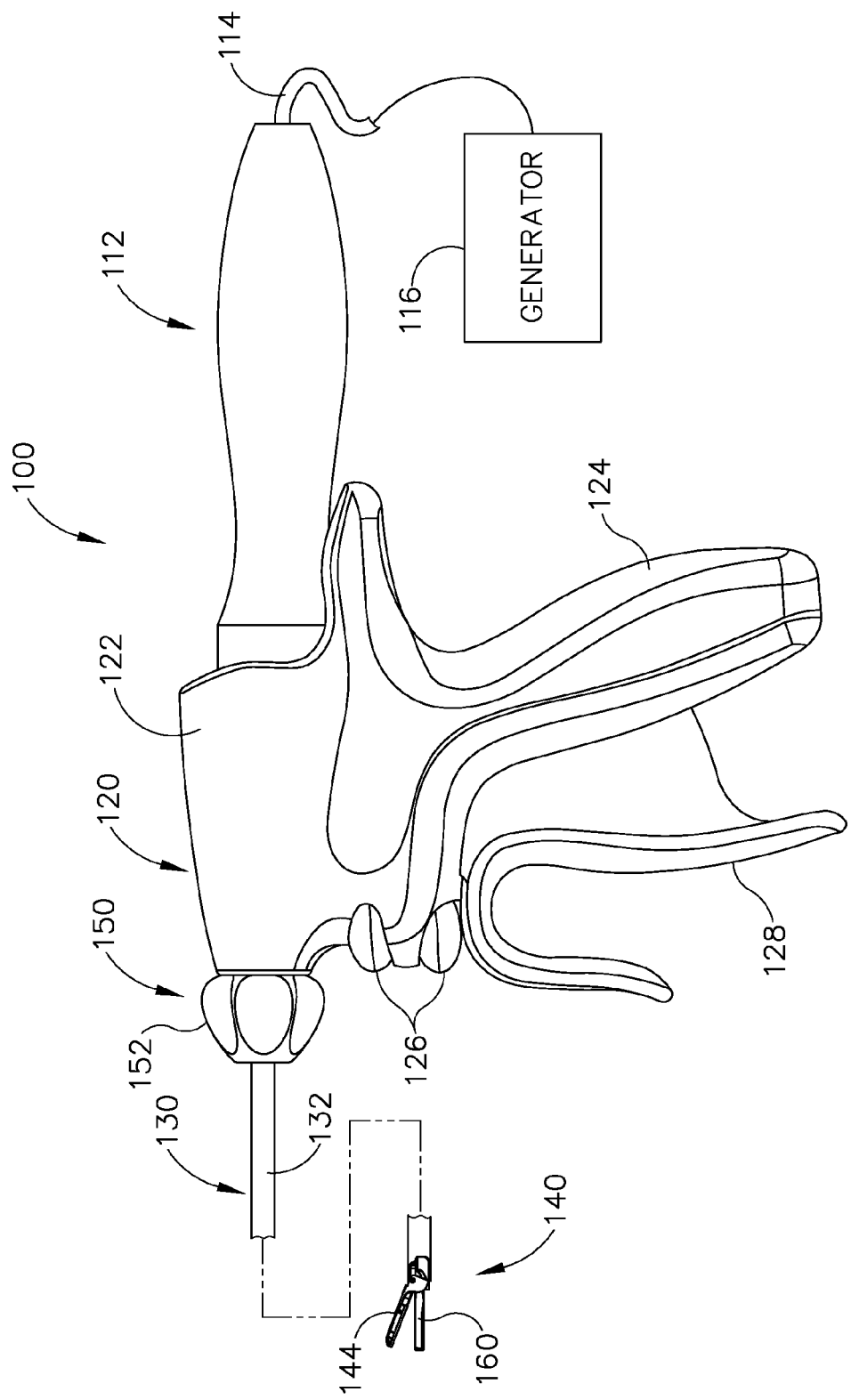
FIG. 2 depicts a side elevational view of an exemplary surgical instrument that may be incorporated into the system of FIG. 1.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, the system (10) comprises an ultrasonic generator (12) and an ultrasonic surgical instrument (20). As will be described in greater detail below, the instrument (20) is operable to cut tissue and seal or weld tissue (e.g., a blood vessel, etc.) substantially simultaneously, using ultrasonic vibrational energy. The generator (12) and the instrument (20) are coupled together via a cable (14). The cable (14) may comprise a plurality of wires; and may provide unidirectional electrical communication from the generator (12) to the instrument (20) and/or bidirectional electrical communication between the generator (12) and the instrument (20). By way of example only, the cable (14) may comprise a "hot" wire for electrical power to the surgical instrument (20), a ground wire, and a signal wire for transmitting signals from the surgical instrument (20) to the ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of the system (10) may incorporate generator the (12) into instrument the (20), such that the cable (14) may simply be omitted.

By way of example only, the generator (12) may comprise the GEN04, GEN11, or GEN 300 sold by Ethicon Endo-Surgery, Inc. of Cincinnati, Ohio. In addition or in the alternative, the generator (12) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. Alternatively, any other suitable generator may be used. As will be described in greater detail below, the generator (12) is operable to provide power to the instrument (20) to perform ultrasonic surgical procedures.

The instrument (20) comprises a handle assembly (22), which is configured to be grasped in one hand (or two hands) of an operator and manipulated by one hand (or two hands) of the operator during a surgical procedure. For instance, in some versions, the handle assembly (22) may be grasped like a pencil by the operator. In some other versions, the handle assembly (22) may include a scissor grip that may be grasped like scissors by the operator. In some other versions, the handle assembly (22) may include a pistol grip that may be grasped like a pistol by the operator. Of course, the handle assembly (22) may be configured to be gripped in any other suitable fashion. Furthermore, some versions of the instrument (20) may substitute the handle assembly (22) with a body that is coupled to a robotic surgical system that is configured to operate the instrument (20) (e.g., via remote control, etc.). In the present example, a blade (24) extends distally from the handle assembly (22). The handle assembly (22) includes an ultrasonic transducer (26) and an ultrasonic waveguide (28), which couples the ultrasonic transducer (26) with the blade (24). The ultrasonic transducer (26) receives electrical power from the generator (12) via the cable (14). By virtue of its piezoelectric properties, the ultrasonic transducer (26) is operable to convert such electrical power into ultrasonic vibrational energy.

The ultrasonic waveguide (28) may be flexible, semi-flexible, rigid, or have any other suitable properties. As noted above, the ultrasonic transducer (26) is integrally coupled with the blade (24) via the ultrasonic waveguide (28). In particular, when the ultrasonic transducer (26) is activated to vibrate at ultrasonic frequencies, such vibrations are communicated through the ultrasonic waveguide (28) to the blade (24), such that the blade (24) will also vibrate at ultrasonic frequencies. When the blade (24) is in an activated state (i.e., vibrating ultrasonically), the blade (24) is operable to effectively cut through tissue and seal tissue. The ultrasonic transducer (26), the ultrasonic waveguide (28), and the blade (24) together thus form an acoustic assembly providing ultrasonic energy for surgical procedures when powered by the generator (12). The handle assembly (22) is configured to substantially isolate the operator from the vibrations of the acoustic assembly formed by the transducer (26), the ultrasonic waveguide (28), and the blade (24).

In some versions, the ultrasonic waveguide (28) may amplify the mechanical vibrations transmitted through the ultrasonic waveguide (28) to blade (24). The ultrasonic waveguide (28) may further have features to control the gain of the longitudinal vibration along the ultrasonic waveguide (28) and/or features to tune the ultrasonic waveguide (28) to the resonant frequency of the system (10). For instance, the ultrasonic waveguide (28) may have any suitable cross-sectional dimensions/configurations, such as a substantially uniform cross-section, be tapered at various sections, be tapered along its entire length, or have any other suitable configuration. The ultrasonic waveguide (28) may, for example, have a length substantially equal to an integral number of one-half system wavelengths ($n\lambda/2$). The ultrasonic waveguide (28) and the blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of the blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When the transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When the transducer (26) of the present example is activated, these mechanical oscillations are transmitted through the waveguide (28) to reach blade (24), thereby providing oscillation of the blade (24) at the resonant ultrasonic frequency. Thus, the ultrasonic oscillation of the blade (24) may simultaneously sever the tissue and denature the proteins in adjacent tissue cells, thereby providing a coagulative effect with relatively little thermal spread. In some versions, an electrical current may also be provided through the blade (24) to also cauterize the tissue.

By way of example only, the ultrasonic waveguide (28) and the blade (24) may comprise components sold under product codes SNGHK and SNGCB by Ethicon Endo-Surgery, Inc. of Cincinnati, Ohio. By way of further example only, the ultrasonic waveguide (28) and/or the blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, the ultrasonic waveguide (28) and/or the blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of the ultrasonic waveguide (28) and the blade (24) will be apparent to those of ordinary skill in the art in view of the teachings herein.

The handle assembly (22) of the present example also includes a control selector (30) and an activation switch (32), which are each in communication with a circuit board (34). By way of example only, the circuit board (34) may comprise a conventional printed circuit board, a flex circuit, a rigid-flex circuit, or may have any other suitable configuration. The control selector (30) and the activation switch (32) may be in communication with the circuit board (34) via one or more wires, traces formed in a circuit board or flex circuit, and/or in any other suitable fashion. The circuit board (34) is coupled with the cable (14), which is in turn coupled with the control circuitry (16) within the generator (12). The activation switch (32) is operable to selectively activate power to the ultrasonic transducer (26). In particular, when the switch (32) is activated, such activation provides communication of appropriate power to the ultrasonic transducer (26) via the cable (14). By way of example only, the activation switch (32) may be constructed in accordance with any of the teachings of the various references cited herein. Other various forms that the activation switch (32) may take will be apparent to those of ordinary skill in the art in view of the teachings herein.

In the present example, the surgical system (10) is operable to provide at least two different levels or types of ultrasonic energy (e.g., different frequencies and/or amplitudes, etc.) at the blade (24). To that end, the control selector (30) is operable to permit the operator to select a desired level/amplitude of ultrasonic energy. By way of example only, the control selector (30) may be constructed in accordance with any of the teachings of the various references cited herein. Other various forms that the control selector (30) may take will be apparent to those of ordinary skill in the art in view of the teachings herein. In some versions, when an operator makes a selection through the control selector (30), the operator's selection is communicated back to the control circuitry (16) of the generator (12) via the cable (14), and the control circuitry (16) adjusts the power communicated from the generator (12) accordingly the next time the operator actuates the activation switch (32).

It should be understood that the level/amplitude of ultrasonic energy provided at the blade (24) may be a function of characteristics of the electrical power communicated from the generator (12) to the instrument (20) via the cable (14). Thus, control circuitry (16) of the generator (12) may provide electrical power (via the cable (14)) having characteristics associated with the ultrasonic energy level/amplitude or type selected through control the selector (30). The generator (12) may thus be operable to communicate different types or degrees of electrical power to the ultrasonic transducer (26), in accordance with selections made by the operator via the control selector (30). In particular, and by way of example only, the generator (12) may increase the voltage and/or current of the applied signal to increase the longitudinal amplitude of the acoustic assembly. As a merely illustrative example, the generator (12) may provide selectability between a "level 1" and a "level 5," which may correspond with the blade (24) vibrational resonance amplitude of approximately 50 microns and approximately 90 microns, respectively. Various ways in which the control circuitry (16) may be configured will be apparent to those of ordinary skill in the art in view of the teachings herein. It should also be understood that the control selector (30) and the activation switch (32) may be substituted with two or more activation switches (32). In some such versions, one activation switch (32) is operable to activate the blade (24) at one power level/type while another activation switch (32) is operable to activate the blade (24) at another power level/type, etc.

In some alternative versions, the control circuitry (16) is located within the handle assembly (22). For instance, in some such versions, the generator (12) only communicates one type of electrical power (e.g., just one voltage and/or current available) to the handle assembly (22), and the control circuitry (16) within the handle assembly (22) is operable to modify the electrical power (e.g., the voltage of the electrical power), in accordance with selections made by the operator via the control selector (30), before the electrical power reaches the ultrasonic transducer (26). Furthermore, the generator (12) may be incorporated into the handle assembly (22) along with all other components of the surgical system (10). For instance, one or more batteries (not shown) or other portable sources of power may be provided in the handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations of the surgical instrument (20). It should be understood that the various examples of the surgical instrument (20) described below may be readily incorporated into the surgical system (10) as described above. It should also be understood that the various components and operabilities of the surgical instrument (20) described above may be readily incorporated into the exemplary versions of the surgical instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-5 illustrate an exemplary ultrasonic surgical instrument (100). At least part of the surgical instrument (100) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 8,461,744; U.S. Pat. No. 8,623,027; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071, issued May 5, 2015; U.S. Pub. No. 2012/0112687, now U.S. Pat. No. 9,381,058, issued Jul. 5, 2016; U.S. Pub. No. 2012/0116265; U.S. Pub. No. 2014/0005701, now U.S. Pat. No. 9,393,037, issued Jul. 19, 2016; U.S. Pub. No. 2014/0114334, now U.S. Pat. No. 9,095,367, issued Aug. 4, 2015; U.S. Pat. App. No. 61/410,603; and/or U.S. Pub. No. 2015/0080924, published Mar. 19, 2015. The disclosures of each of the foregoing patents, publications, and applications are incorporated by reference herein. As described therein and as will be described in greater detail below, the surgical instrument (100) is operable to cut tissue and seal or weld tissue (e.g., a blood vessel, etc.) substantially simultaneously. It should also be understood that the surgical instrument (100) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the surgical instrument (100) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to the surgical instrument (100), there is no intent for any of the description herein to be presumed as admitted prior art.

Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

The surgical instrument (100) of the present example comprises a handle assembly (120), a shaft assembly (130), and an end effector (140). The handle assembly (120) comprises a body (122) including a pistol grip (124) and a pair of buttons (126). The handle assembly (120) also includes a trigger (128) that is pivotable toward and away from the pistol grip (124). It should be understood, however, that various other suitable configurations may be used, including but not limited to a pencil-grip configuration or a scissor-grip configuration. The end effector (140) includes an ultrasonic blade (160) and a pivoting clamp arm (144). The clamp arm (144) is coupled with the trigger (128) such that the clamp arm (144) is pivotable toward the ultrasonic blade (160) in response to pivoting of the trigger (128) toward the pistol grip (124); and such that the clamp arm (144) is pivotable away from the ultrasonic blade (160) in response to pivoting of the trigger (128) away from the pistol grip (124). Various suitable ways in which the clamp arm (144) may be coupled with the trigger (128) will be apparent to those of ordinary skill in the art in view of the teachings herein. In some versions, one or more resilient members are used to bias the clamp arm (144) and/or the trigger (128) to the open position shown in FIG. 4.

An ultrasonic transducer assembly (112) extends proximally from the body (122) of the handle assembly (120). The transducer assembly (112) is coupled with a generator (116) via a cable (114). The transducer assembly (112) receives electrical power from the generator (116) and converts that power into ultrasonic vibrations through piezoelectric principles. The generator (116) may include a power source and control module configured to provide a power profile to the transducer assembly (112) that is particularly suited for the generation of ultrasonic vibrations through the transducer assembly (112). By way of example only, the generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of the generator (116) may be integrated into the handle assembly (120), and that the handle assembly (120) may even include a battery or other on-board power source such that the cable (114) is omitted. Still other suitable forms that the generator (116) may take, as well as various features and operabilities that the generator (116) may provide, will be apparent to those of ordinary skill in the art in view of the teachings herein.

The blade (160) of the present example is operable to vibrate at ultrasonic frequencies in order to effectively cut through and seal tissue, particularly when the tissue is being clamped between the clamp arm (144) and the blade (160). The blade (160) is positioned at the distal end of an acoustic drivetrain. This acoustic drivetrain includes the transducer assembly (112) and an acoustic waveguide (102). The transducer assembly (112) includes a set of piezoelectric discs (not shown) located proximal to a horn (not shown) of the rigid acoustic waveguide (102). The piezoelectric discs are operable to convert electrical power into ultrasonic vibrations, which are then transmitted along the acoustic waveguide (102), which extends through the shaft assembly (130), to the blade (160) in accordance with known configurations and techniques. By way of example only, this portion of the acoustic drivetrain may be configured in accordance with various teachings of various references that are cited herein.

The waveguide (102) is secured within the shaft assembly (130) via a pin (133), which passes through the waveguide (102) and the shaft assembly (130). The pin (133) is located at a position along the length of the waveguide (102) corresponding to a node associated with resonant ultrasonic vibrations communicated through the waveguide (102). When the ultrasonic blade (160) is in an activated state (i.e., vibrating ultrasonically), the ultrasonic blade (160) is operable to effectively cut through and seal tissue, particularly when the tissue is being clamped between the clamp arm (144) and the ultrasonic blade (160). It should be understood that the waveguide (102) may be configured to amplify mechanical vibrations transmitted through the waveguide (102). Furthermore, the waveguide (102) may include features operable to control the gain of the longitudinal vibrations along the waveguide (102) and/or features to tune the waveguide (102) to the resonant frequency of the system.

In the present example, the distal end of the blade (160) is located at a position corresponding to an anti-node associated with resonant ultrasonic vibrations communicated through the waveguide (102), in order to tune the acoustic assembly to a preferred resonant frequency $f_o$ when the acoustic assembly is not loaded by tissue. When the transducer assembly (112) is energized, the distal end of the blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When the transducer assembly (112) of the present example is activated, these mechanical oscillations are transmitted through the waveguide (102) to reach the blade (160), thereby providing oscillation of the blade (160) at the resonant ultrasonic frequency. Thus, when tissue is secured between the blade (160) and the clamp arm (144), the ultrasonic oscillation of the blade (160) may simultaneously sever the tissue and denature the proteins in adjacent tissue cells, thereby providing a coagulative effect with relatively little thermal spread. In some versions, an electrical current may also be provided through the blade (160) and the clamp arm (144) to also cauterize the tissue. While some configurations for an acoustic transmission assembly and the transducer assembly (112) have been described, still other suitable configurations for an acoustic transmission assembly and the transducer assembly (112) will be apparent to one or ordinary skill in the art in view of the teachings herein. Similarly, other suitable configurations for the end effector (140) will be apparent to those of ordinary skill in the art in view of the teachings herein.

An operator may activate the buttons (126) to selectively activate the transducer assembly (112) to activate the blade (160). In the present example, two buttons (126) are provided—one for activating the blade (160) at a low power and another for activating the blade (160) at a high power. However, it should be understood that any other suitable number of buttons and/or otherwise selectable power levels may be provided. For instance, a foot pedal may be provided to selectively activate the transducer assembly (112). The buttons (126) of the present example are positioned such that an operator may readily fully operate the instrument (100) with a single hand. For instance, the operator may position their thumb about the pistol grip (124), position their middle, ring, and/or little finger about the trigger (128), and manipulate the buttons (126) using their index finger. Of course, any other suitable techniques may be used to grip and operate the surgical instrument (100); and the buttons (126) may be located at any other suitable positions.

The shaft assembly (130) of the present example comprises an outer sheath (132), an inner tube (134) slidably disposed within the outer sheath (132), and a waveguide (102) disposed within the inner tube (134). As will be discussed in more detail below, the inner tube (134) is operable to translate longitudinally within the outer sheath (132) relative to the outer sheath (132) to selectively pivot the clamp arm (144) toward and away from the blade (160). The shaft assembly (130) of the present example further includes a rotation assembly (150). The rotation assembly (150) is operable to rotate the entire shaft assembly (130) and the end effector (140) relative to the handle assembly (120) about a longitudinal axis of the shaft assembly (130). In some versions, the rotation assembly (150) is operable to selectively lock the angular position of the shaft assembly (130) and the end effector (140) relative to the handle assembly (120) about the longitudinal axis of the shaft assembly (130). For instance, a rotation knob (152) of the rotation assembly (150) may be translatable between a first longitudinal position, in which the shaft assembly (130) and the end effector (140) are rotatable relative to the handle assembly (120) about the longitudinal axis of the shaft assembly (130); and a second longitudinal position, in which the shaft assembly (130) and the end effector (140) are not rotatable relative to the handle assembly (120) about the longitudinal axis of the shaft assembly (130). Of course, the shaft assembly (130) may have a variety of other components, features, and operabilities, in addition to or in lieu of any of those noted above. Other suitable configurations for the shaft assembly (130) will be apparent to those of ordinary skill in the art in view of the teachings herein.

Figure 3:
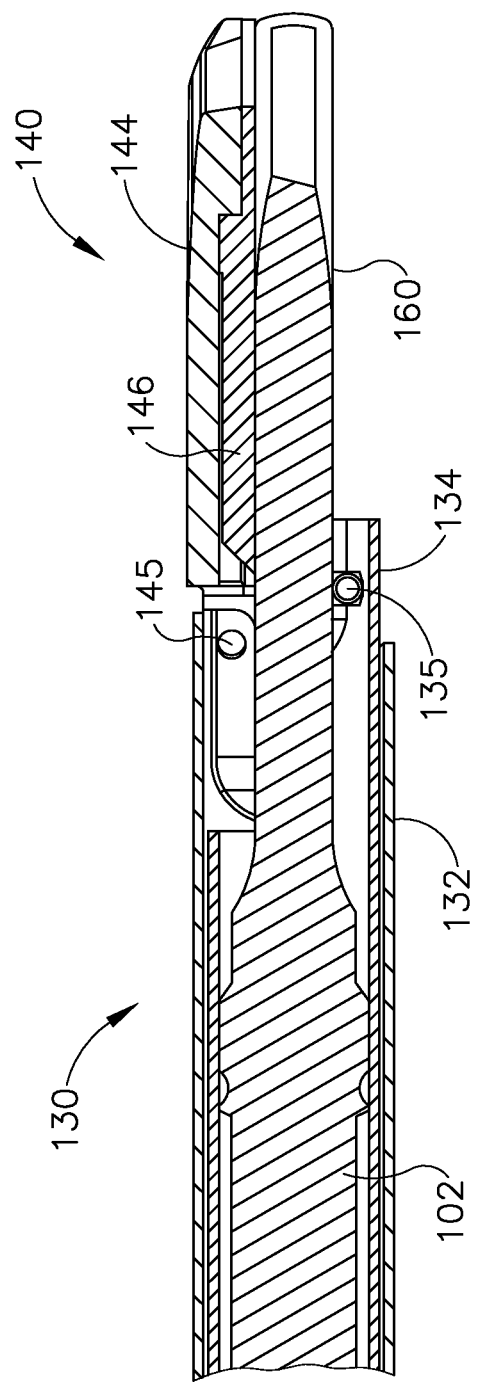
FIG. 3 depicts a cross-sectional side view of an end effector of the instrument of FIG. 2 in a closed configuration.
Figure 4:
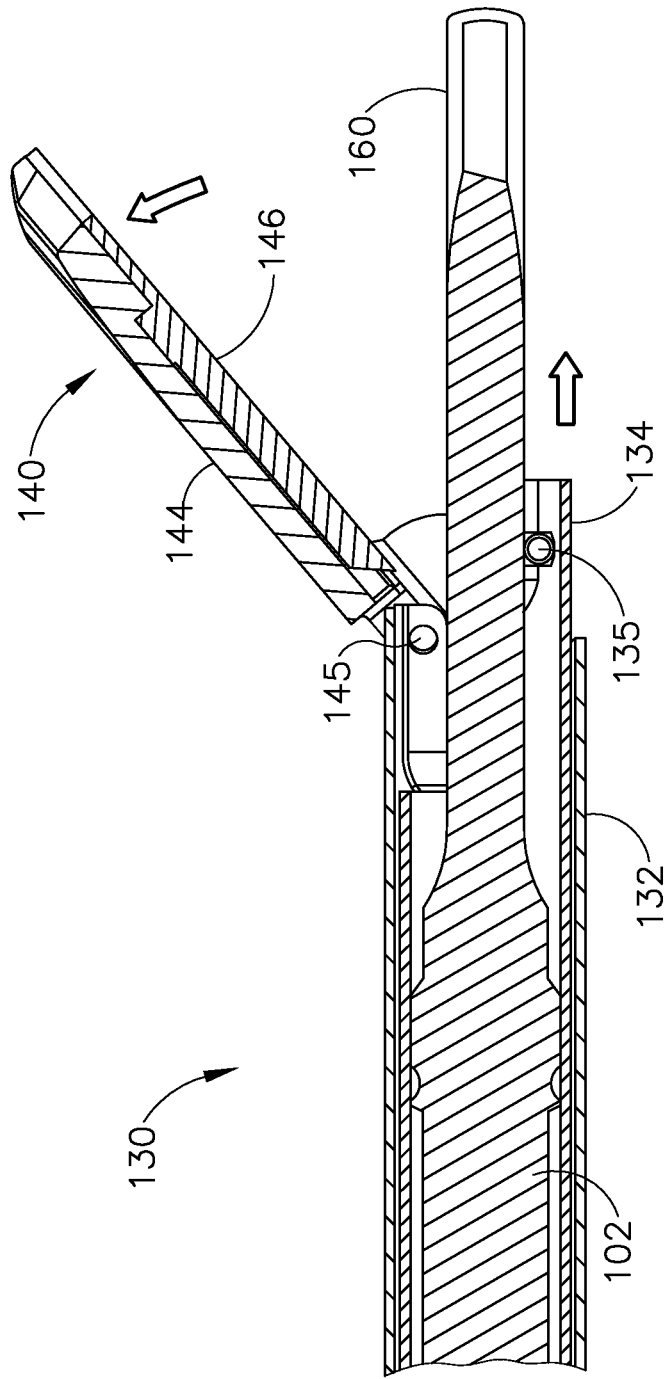
FIG. 4 depicts a cross-sectional side view of the end effector of FIG. 3 in an open configuration.

As shown in FIGS. 3 and 4, the end effector (140) includes the ultrasonic blade (160) and the clamp arm (144). The clamp arm (144) includes a clamp pad (146) secured to an underside of the clamp arm (144) and facing the blade (160). The clamp arm (144) is pivotably coupled with a distal end of the outer sheath (132) of the shaft assembly (130) above the ultrasonic blade (160) via a pin (145). As best seen in FIG. 4, a distal end of the inner tube (134) is rotatably coupled with a proximal end of the clamp arm (144) below the ultrasonic blade (160) via a pin (135) such that longitudinal translation of the inner tube (134) causes rotation of the clamp arm (144) about the pin (145) toward and away from the ultrasonic blade (160) to thereby clamp tissue between the clamp arm (144) and the ultrasonic blade (160) to cut and/or seal the tissue. In particular, proximal longitudinal translation of the inner tube (134) relative to the outer sheath (132) and the handle assembly (120) causes the clamp arm (144) to move toward the ultrasonic blade (160); and distal longitudinal translation of the inner tube (134) relative to the outer sheath (132) and the handle assembly (120) causes the clamp arm (144) to move away from the ultrasonic blade (160).

Figure 5:
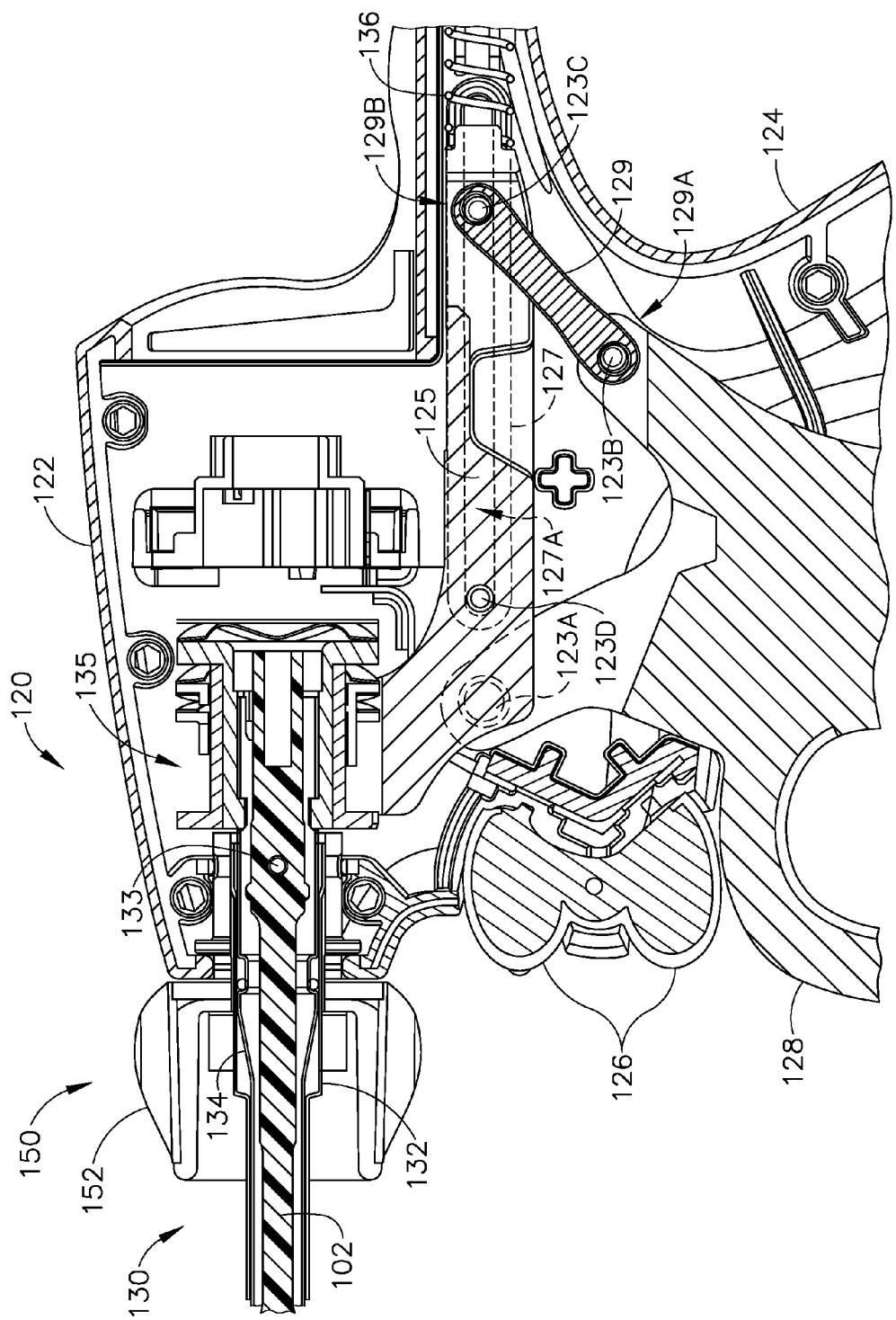
FIG. 5 depicts a cross-sectional side view of a handle assembly of the instrument of FIG. 2.

As shown in FIG. 5, and as discussed above, the trigger (128) is pivotably coupled to the handle assembly (120) via a pin (123A) such that the trigger (128) is operable to rotate about the pin (123A). As will be described in more detail below, the trigger (128) is coupled with a yoke (125) via a linkage (129) such that rotation of the trigger (128) about the pin (123A) causes longitudinal translation of the yoke (125). A first end (129A) of the linkage (129) is rotatably coupled with a proximal portion of the trigger (128) via a pin (123B). A second end (129B) of the linkage (129) is rotatably coupled with a proximal portion of the yoke (125) via a pin (123C). A pair of elongate oval-shaped projections (127) extend inwardly from interior surfaces of the body (122). An interior surface of each oval-shaped projection (127) defines an elongate oval-shaped slot (127A). The pin (123C) passes completely through the proximal portion of the yoke (125) and the second end (129B) of the linkage (129) such that ends of the pin (123C) extend from opposite sides of the yoke (125). These ends of the pin (123C) are slidably and rotatably disposed within the oval-shaped slots (127A). A pin (123D) passes completely through a distal portion of the yoke (125) such that ends of the pin (123D) extend from opposite sides of the yoke (125). These ends of the pin (123D) are slidably and rotatably disposed within the oval-shaped slots (127A). It should therefore be understood that the yoke (125) is longitudinally translatable within the oval-shaped slots (127A) via the pins (123C, 123D) between a proximal longitudinal position and a distal longitudinal position. Furthermore, because the proximal portion of the trigger (128) is coupled with the yoke (125) via the linkage (129), pivoting of the trigger (128) toward and away from the pistol grip (124) will cause longitudinal translation of the yoke (125) within the oval-shaped slots (127A). In particular, pivoting of the trigger (128) toward the pistol grip (124) will cause proximal longitudinal translation of the yoke (125) within the oval-shaped slots (127A); and that pivoting of the trigger (128) away from the pistol grip (124) will cause distal longitudinal translation of the yoke (125) within the oval-shaped slots (127A).

A distal portion of the yoke (125) is coupled with the inner tube (134) of the shaft assembly (130) via a coupling assembly (135). As discussed above, the inner tube (134) is longitudinally translatable within the outer sheath (132), such that the inner tube (134) is configured to longitudinally translate concurrently with the yoke (125). Furthermore, because pivoting of the trigger (128) toward the pistol grip (124) causes proximal longitudinal translation of the yoke (125), it should be understood that pivoting of the trigger (128) toward the pistol grip (124) will cause proximal longitudinal translation of the inner tube (134) relative to the outer sheath (132) and the handle assembly (120); and because pivoting of the trigger (128) away from the pistol grip (124) causes distal longitudinal translation of the yoke (125), it should be understood that and that pivoting of the trigger (128) away from the pistol grip (124) will cause distal longitudinal translation of the inner tube (134) relative to the outer sheath (132) and the handle assembly (120). Finally, because longitudinal translation of the inner tube (134) causes rotation of the clamp arm (144) toward and away from the blade (160) as discussed above, it should be understood that pivoting of the trigger (128) toward the pistol grip (124) will cause the clamp arm (144) to move toward the ultrasonic blade (160); and that pivoting of the trigger (128) away from the pistol grip (124) will cause the clamp arm (144) to move away from the ultrasonic blade (160).

In some versions, one or more resilient members are used to bias the clamp arm (144) and/or the trigger (128) to the open position shown in FIG. 4. For instance, as shown in FIG. 5, a spring (136) is positioned within a proximal end of the body (122) of the handle assembly (120). The spring (136) bears against the body (122) and a proximal end of the yoke (125) to thereby bias the yoke (125) toward the distal position. Biasing of the yoke (125) toward the distal position causes the inner tube (134) to be biased distally and further causes the trigger (128) to be biased away from the pistol grip (124).

The foregoing components and operabilities of the surgical instrument (100) are merely illustrative. The surgical instrument (100) may be configured in numerous other ways as will be apparent to those of ordinary skill in the art in view of the teachings herein. By way of example only, at least part of the surgical instrument (100) may be constructed and/or operable in accordance with at least some of the teachings of any of the following, the disclosures of which are all incorporated by reference herein: U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071, issued May 5, 2015; U.S. Pub. No. 2011/0015660, now U.S. Pat. No. 8,461,744, issued Jun. 11, 2013; U.S. Pub. No. 2012/0112687, now U.S. Pat. No. 9,381,058, issued Jul. 5, 2016; U.S. Pub. No. 2012/0116265; U.S. Pub. No. 2014/0005701, now U.S. Pat. No. 9,393,037, issued Jul. 19, 2016 and/or U.S. Pub. No. 2014/0114334, now U.S. Pat. No. 9,095,367, issued Aug. 4, 2015. Additional merely illustrative variations for the surgical instrument (100) will be described in greater detail below. It should be understood that the below described variations may be readily applied to the surgical instrument (100) described above and any of the instruments referred to in any of the references that are cited herein, among others.

III. Exemplary Clamp Arm with Replaceable Clamp Pad

Those of ordinary skill in the art will recognize that the clamp pad (146) may experience a substantial amount of wear and dear during use of the end effector (140). For instance, the clamp pad (146) may be formed of a polytetrafluoroethylene (PTFE) material. The clamp pad (146) may encounter heat, compression forces, and vibrations generated via the blade (160), which may work together to eventually wear out the material forming the clamp pad (146). It may therefore be desirable to provide a version of the end effector (140) where the clamp pad (146) is replaceable. In particular, it may be desirable to enable replacement of the clamp pad (146) without necessarily also having to replace the clamp arm (144) and/or other components of the end effector (140).

Figure 6A:
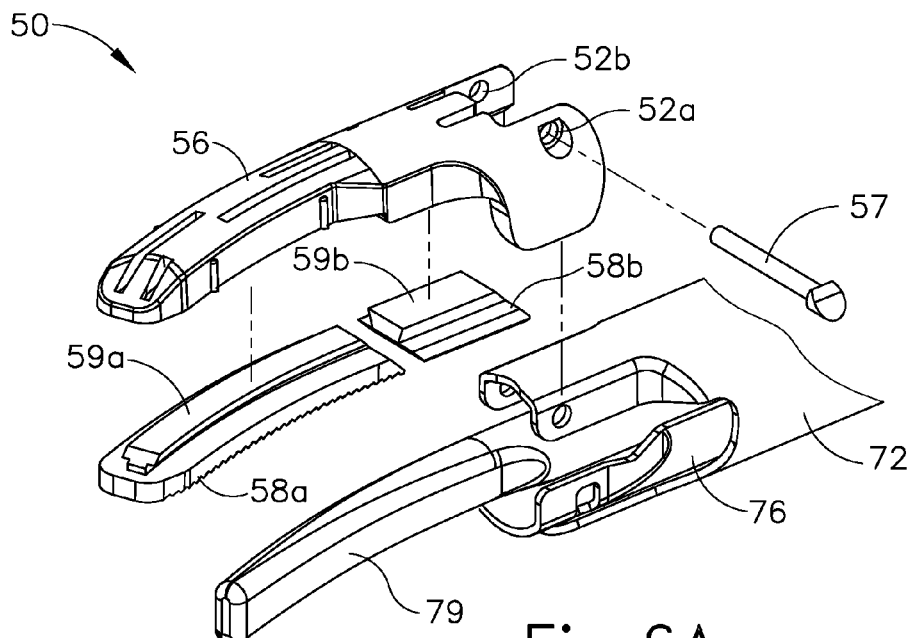
FIG. 6A depicts an exploded perspective view of an exemplary end effector that may be incorporated into the instrument of FIG. 2, with a clamp arm in a first position.
Figure 6B:
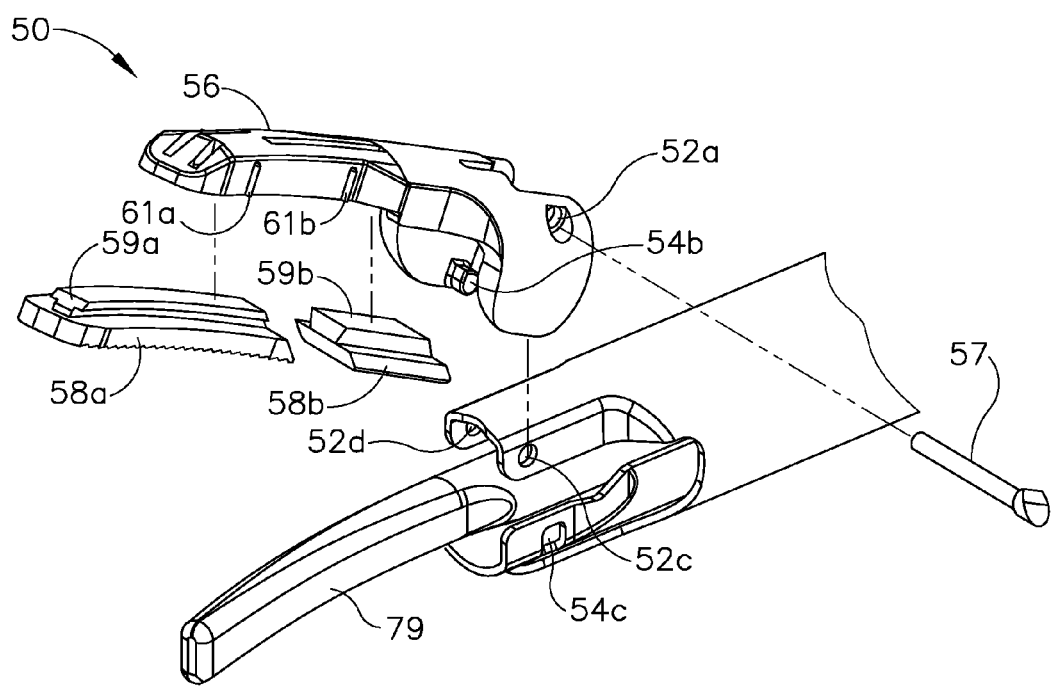
FIG. 6B depicts an exploded perspective view of the end effector of FIG. 6A, with the clamp arm in a second position.
Figure 7:
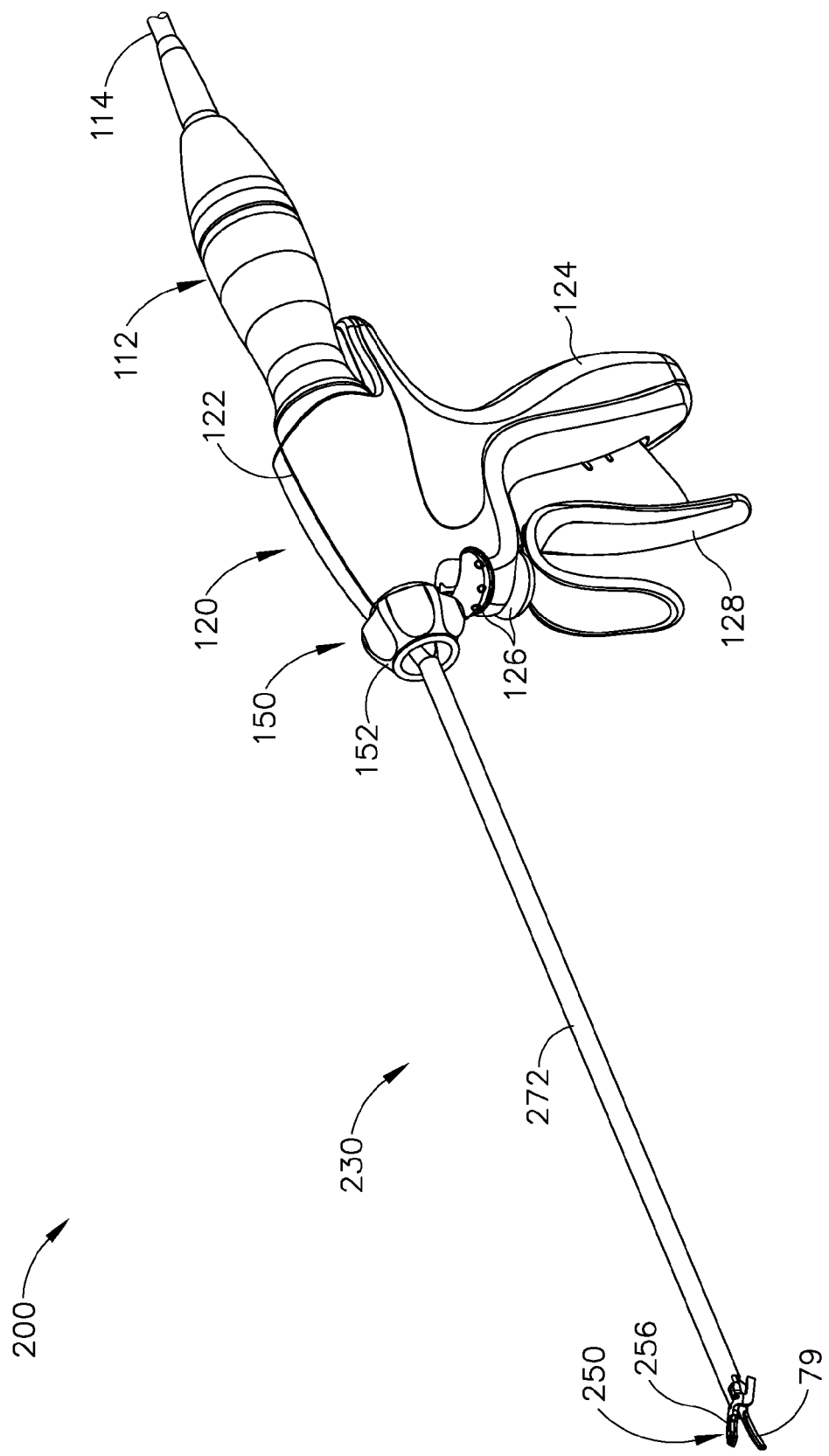
FIG. 7 depicts a perspective view of another exemplary surgical instrument that may be incorporated into the system of FIG. 1.

FIGS. 6A-6B show an exemplary end effector (50) with a clamp arm (56) and replaceable clamp pads (58a, 58b). The end effector (50) may be readily incorporated into the surgical instrument (20, 100) described above. The end effector (50) further includes an outer sheath (72), an inner tube (76), an ultrasonic blade (79), and a pivot pin (57). The outer sheath (72), the inner tube (76), and the blade (79) are substantially similar to the outer sheath (132), the inner tube (134) and the ultrasonic blade (160), respectively, discussed above.

The clamp arm (56) includes coupling holes (52a, 52b) that are configured to receive the pivot pin (57). The clamp arm (56) is pivotally coupled to the outer sheath (72) via the pivot pin (57). The clamp arm (56) is pivotally coupled to the inner tube (76) via integral studs (54b), which are disposed in openings (54c) of the inner tube (76). Clamp pads (58a, 58b) further include tapered tenons (59a, 59b) that are configured to mate with complementary mortises (not shown) defined by the clamp arm (56). The tenons (59a, 59b) are configured to slide within mortises (not shown) at the proximal end of the clamp arm (56) when the clamp arm (56) is detached from the outer sheath (72). Therefore, when the clamp arm (56), with the assembled clamp pads (58a, 58b), is attached to the outer sheath (72) via the pivot pin (57), the pivot pin (57) prevents the clamp pads (58a, 58b) from sliding proximally relative to the clamp arm (56). In other words, the pivot pin (57) and the closed distal end of the clamp arm (56) confine the clamp pads (58a, 58b) within the mortise via the tenons (59a, 59b), with the pivot pin (57) and the closed distal end of the clamp arm (56) cooperating to act as longitudinal stops.

When the clamp arm (56) is assembled to the outer sheath (72), the clamp pads (58a, 58b) may be fixed relative to the clamp arm (56). However, after a surgical procedure, the clamp pads (58a, 58b) may be removed from the clamp arm (56) by removing the pivot pin (57) to decouple the clamp arm (56) and the outer sheath (72). Once the pivot pin (57) is removed from the coupling holes (52a, 52b), the clamp arm (56) may be removed from the outer sheath (72), which enables the clamp pads (58a, 58b) to slide relative to the clamp arm (56) in the proximal direction. Once sufficiently worn, the used clamp pads (58a, 58b) may then be removed and replaced with new clamp pads (58a, 58b) with similar qualities. Then, the assembled clamp arm (56) with the new clamp pads (58a, 58b) may be coupled to the outer sheath (72) via the pivot pin (57), thereby fixing the clamp pads (58a, 58b) relative to the clamp arm (56). By way of example only, the end effector (50) may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

IV. Exemplary Surgical Instrument with a Positive Stop Clamp Arm

While the end effector (50) allows for replacement of the clamp pads (58a, 58b), the clamp pads (58a, 58b) remain prone to heat, compression forces, and vibrations generated via the blade (79) that tend to expedite deterioration of the material forming the clamp pads (58a, 58b). It may therefore be desirable to provide a version of the end effector (50) that reduces direct contact between the blade (79) and the clamp pads (58a, 58b) or otherwise maintains at least a minimum gap distance between the blade (79) and the clamp pads (58a, 58b), in order to reduce the deleterious effects of heat, compression forces, and vibrations. As such, the useful life of the clamp pads (58a, 58b) may increase while the frequency of replacing the clamp pads (58a, 58b) decreases, thereby saving time and/or costs associated with servicing the surgical instruments (20, 100).

FIGS. 7-9B show an exemplary surgical instrument (200) having an end effector (250) with a positive stop clamp arm (256) configured to maintain at least a minimum gap distance between the clamp pads (58a, 58b) and the blade (79). The end effector (250) may be readily incorporated into the surgical instruments (20, 100) described above. The surgical instrument (200) of this example further includes an outer sheath (272), an inner tube (276), the ultrasonic blade (79), and the pivot pin (57). To this end, like numbers indicate like features discussed above in greater detail. It should therefore be understood that surgical instrument (200) may be configured and operable just like surgical instruments (20, 100), except for the configuration of end effector (250) as described in greater detail below. Generally, the outer sheath (272) and the inner tube (276) are substantially similar in operation to the outer sheath (72) and the inner tube (76) discussed above. However, the connections between the positive stop clamp arm (256), the outer sheath (272), and the inner tube (276) differ from the outer sheath (72) and the inner tube (76) in order to accommodate the exemplary positive stop claim arm (256).

The clamp arm (256) selectively moves from an open position (shown in FIGS. 7-8A and 9A) toward the blade (79) to a closed position (shown in FIGS. 8B and 9B) by selective manipulation of the trigger (128). The clamp arm (256) operatively connects to the trigger (128) by an actuator (280) extending therebetween. In the present example, the actuator (280) includes a push-pull cable assembly (282) and the inner tube (276). Push-pull cable assembly (282) acts as a linkage between inner tube (276) and clamp arm (256) in this example. Push-pull cable assembly (282) may be replaced by a linkage made, for example, by stamping or its function may be incorporated as an extension of the actuator (e.g., inner tube (276)). As discussed above, the inner tube (276) selectively translates within the outer sheath (272) in response to pivotal movement of the trigger (128), which is connected to a proximal end of the inner tube (276). In addition, the push-pull cable assembly (282) is connected to a distal end of the inner tube (276). The push-pull cable extends distally from the inner tube (276) and connects to the proximal end of clamp arm (256) for selectively pivoting the clamp arm (256). As such, the push-pull cable assembly (282) is configured to direct movement of the clamp arm (256) to the closed position when push-pull cable assembly (282) is pulled proximally in tension by the inner tube (276); and to direct movement of clamp arm (256) to the open position when push-pull cable assembly (282) is pushed distally in compression by the inner tube (276). In contrast with the outer sheath (72) (see FIG. 6A) and the inner tube (76) (see FIG. 6A), the outer sheath (272) includes a distal channel (284) and the inner tube (276) terminates proximally from the distal channel (284) so as to collectively accommodate movement of the clamp arm (256).

Figure 8A:
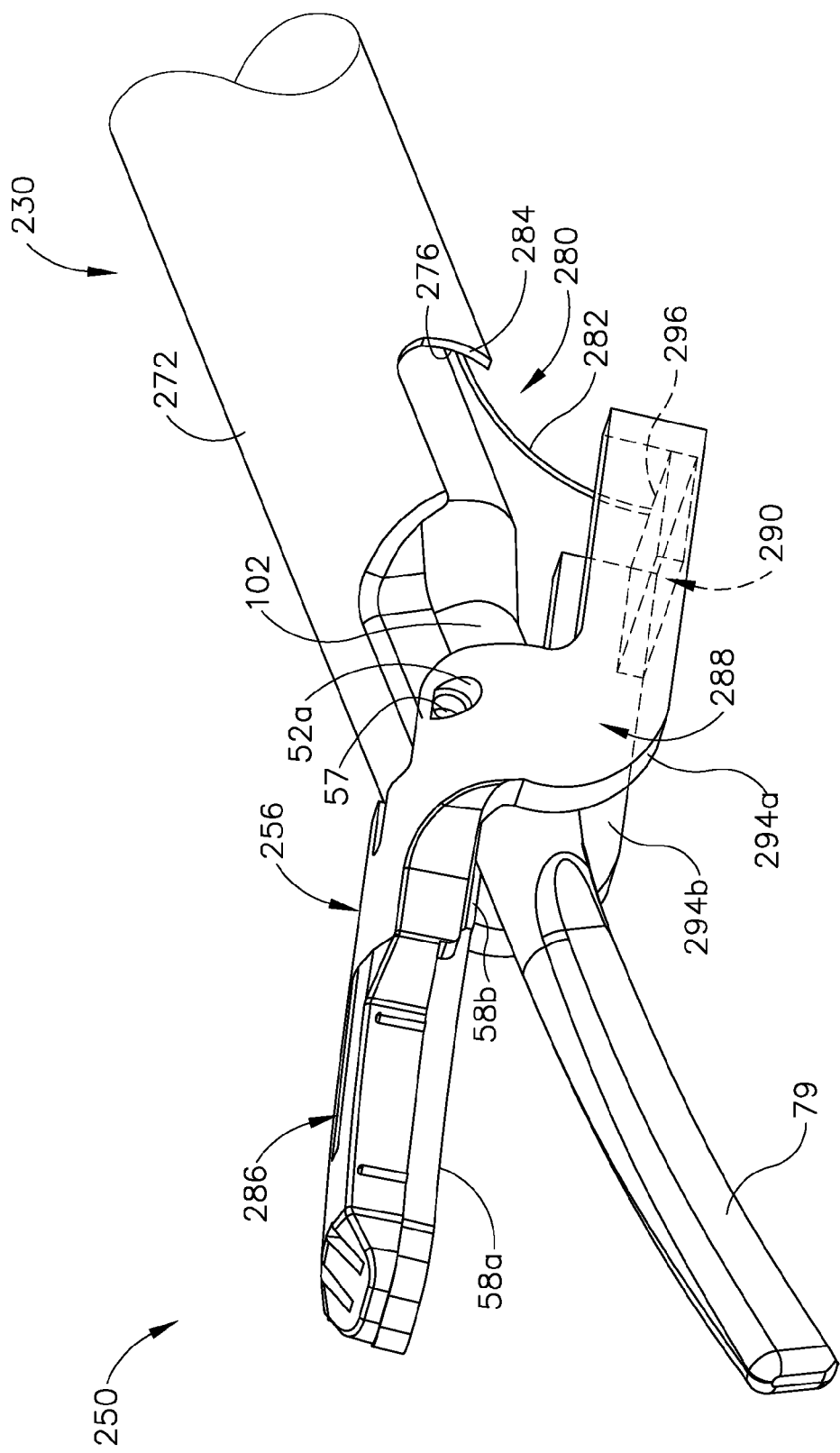
FIG. 8A depicts an enlarged perspective view of the end effector FIG. 7 in an open configuration.
Figure 8B:
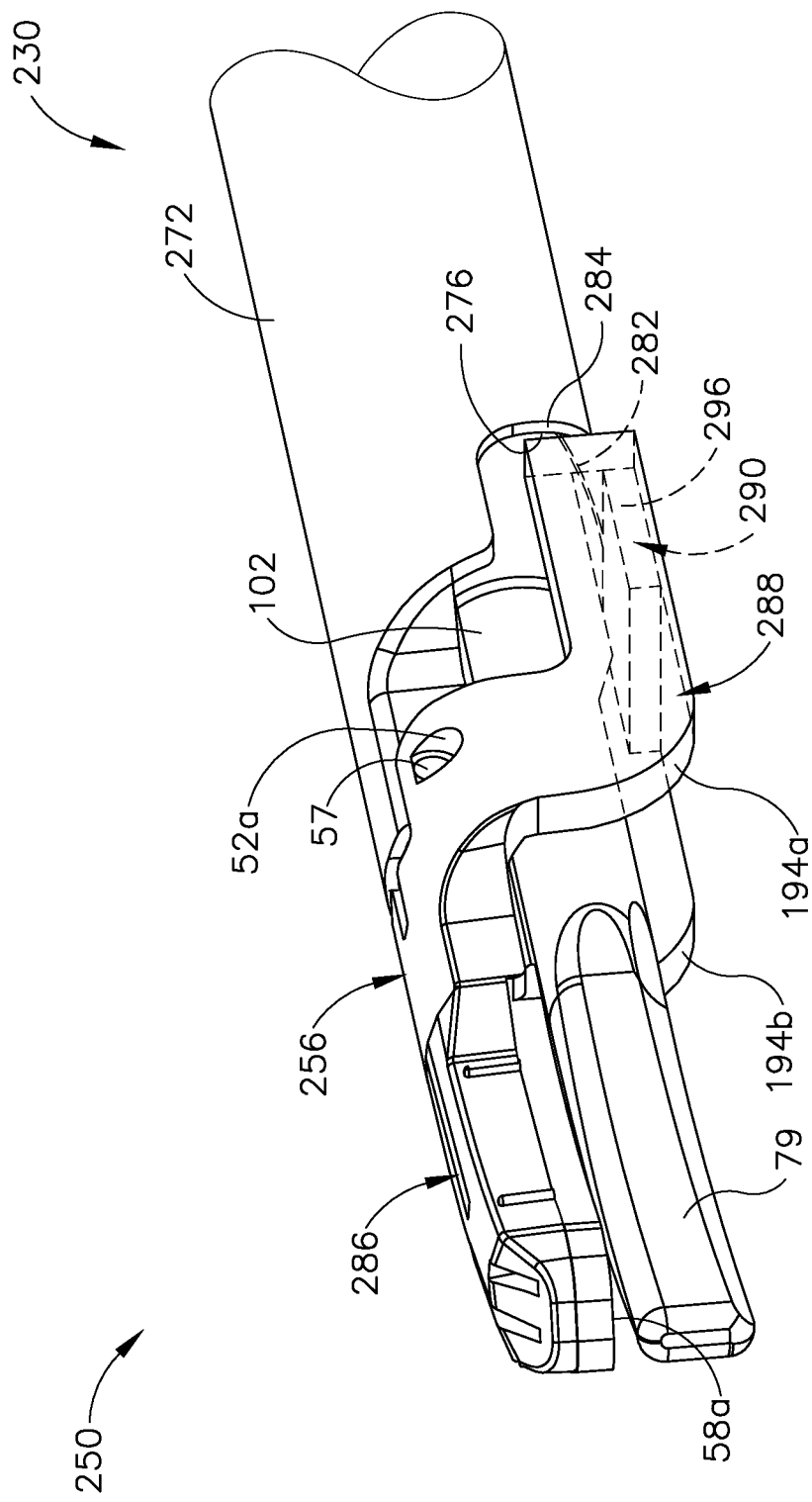
FIG. 8B depicts an enlarged perspective view of the end effector FIG. 7 in a closed configuration.

With respect to the positive stop clamp arm (256), FIGS. 8A-8B respectively show the end effector (250) in the open and closed positions by actuation of the push-pull cable assembly (282). In the present example, the clamp arm (256) pivots about a pivot axis of the pivot pin (57) and generally includes a distal arm portion (286) like that of the clamp arm (56) described above. However, the clamp arm (256) further includes a proximal arm portion (288) that has an abutment (290). The abutment (290) is configured to engage the waveguide (102) in the closed position and inhibit movement of the clamp arm (256) toward the waveguide (102) beyond the closed position. Thereby, the abutment (290) inhibits, or even prevents, the clamp pads (58a, 58b) from directly contacting the blade (79) by maintaining a minimum gap (292) (see FIG. 9B) between the clamp pads (58a, 58b) and the blade (79). By maintaining this minimum gap, clamp pads (58a, 58b) will last longer during a surgical procedure because they will not receive the kind of exposure to wear and tear from blade (79) that they otherwise would have in the absence of the minimum gap.

Alternatively, the design could be such as to allow the gap (292) to be zero, that is, the clamp pad or pads (58a or 58b) could fully close against blade (79) and the function of the abutment (290) then is to limit wear of clamp pad or pads (58a or 58b) by reducing the rate at which clamp pads (58a or 58b) wear due to abutment (290) being fabricated from materials that are more robust than pad or pads (58a or 58b) and/or due to the abutment (290) engaging the blade (79) or waveguide (102) at a location of relatively low displacement (i.a., at or near a nodal position). By way of example only, this location of engagement may have a local displacement of less than 50% of the tip displacement of the blade (79) and more particularly less than 30% of the tip displacement of the blade (79). In addition to the advantage of limiting wear of clamp pad or pads (58a and/or 58b), the proximal engagement by abutment (290) may reduce heat or residual thermal energy in the tissue effecting portion of the end effector (250) by locating the abutment (290) proximal to this tissue effecting region.

The proximal arm portion (288) further includes a pair of support members (294a, 294b) configured to rigidly support the abutment (290) relative to the waveguide (102). Each support member (294a, 294b) is generally L-shaped and extends below the waveguide (102) and proximally from the pivot axis of the pivot pin (57). The abutment (290) extends rigidly between the free proximal ends of the pair of support members (294a, 294b) in order to engage the waveguide (102), which is positioned directly above the abutment (290). In the present example, the abutment (290) includes an upper face in the form of an engagement clamp pad (296). The engagement clamp pad (296) is configured to soften engagement with the waveguide (102) and generally provide a dampening effect between the clamp arm (256) and the waveguide (102) when in the closed position.

By way of example only, clamp pad (296) may comprise a high temperature compatible, low wear, low friction material including polymers, elastomers, metals and ceramics or coated or filled versions thereof such as polytetrafluoroethylene, graphite-filled polytetrafluoroethylene, polyimide, fluorinated ethylene propylene, silicone, and/or any other suitable material (or combination of materials) as will be apparent to those of ordinary skill in the art in view of the teachings herein. By way of further example only, clamp pad (296) may further include fillers such as polytetrafluoroethylene, carbon, molybdenum disulfide, glass, metals (stainless, bronze, etc.), or calcium fluoride. By way of further example only, clamp pad (296) may further include one or more coatings such as FEP- or PTFE-based coatings. By way of further example only, clamp pad (296) may further comprise one or more ceramics such as alumina, zirconia, carbides, or nitrides. By way of further example only, clamp pad (296) may further comprise one or more polymers such as polyaryletherketone (PAEK) family of thermoplastics including PEEK, PEK, PEKK, PEEKK, PEKEKK and blends with other polymers such as PBI or fillers such as PTFE, graphite, carbon, molybdenum disulfide; polyimide and polyimide with fillers such as PTFE, graphite, carbon, molybdenum disulfide; PBI and PBI blended with other polymers; PTFE and PTFE with fillers such as graphite, carbon, molybdenum disulfide, glass, metalics (stainless, bronze, etc.), calcium fluoride; PPS; Polybenzimidazole-Polyetherketoneketone (PBI-PEKK); perfluoroalkoxy (PFA); glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos NanoTool. By way of further example only, clamp pad (296) may further include one or more elastomers such as silicones. Still other suitable materials that may be used to form clamp pad (296) will be apparent to those of ordinary skill in the art in view of the teachings herein.

Figure 9A:
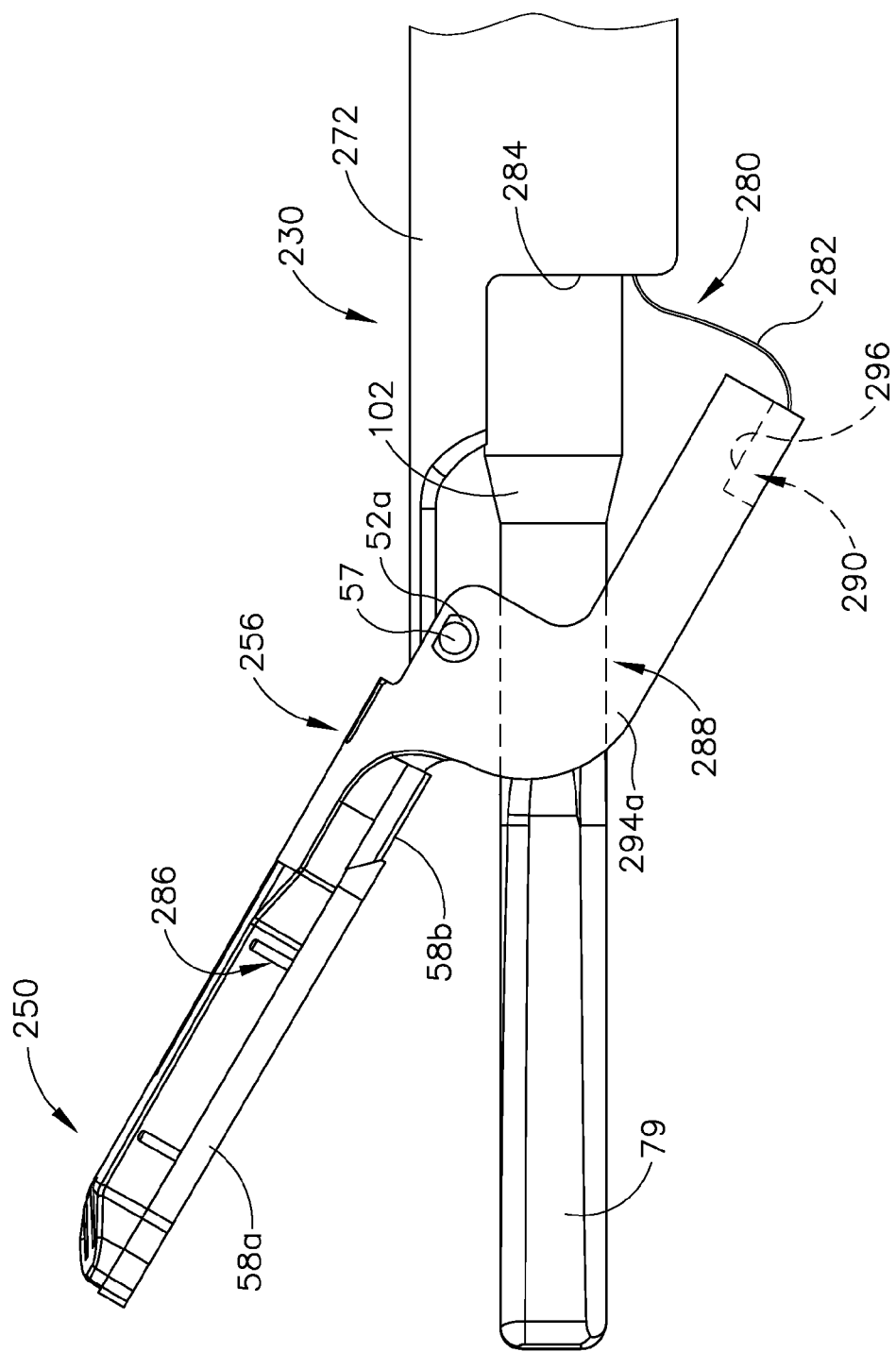
FIG. 9A depicts a an enlarged side view of the end effector of FIG. 7 in the open configuration.
Figure 9B:
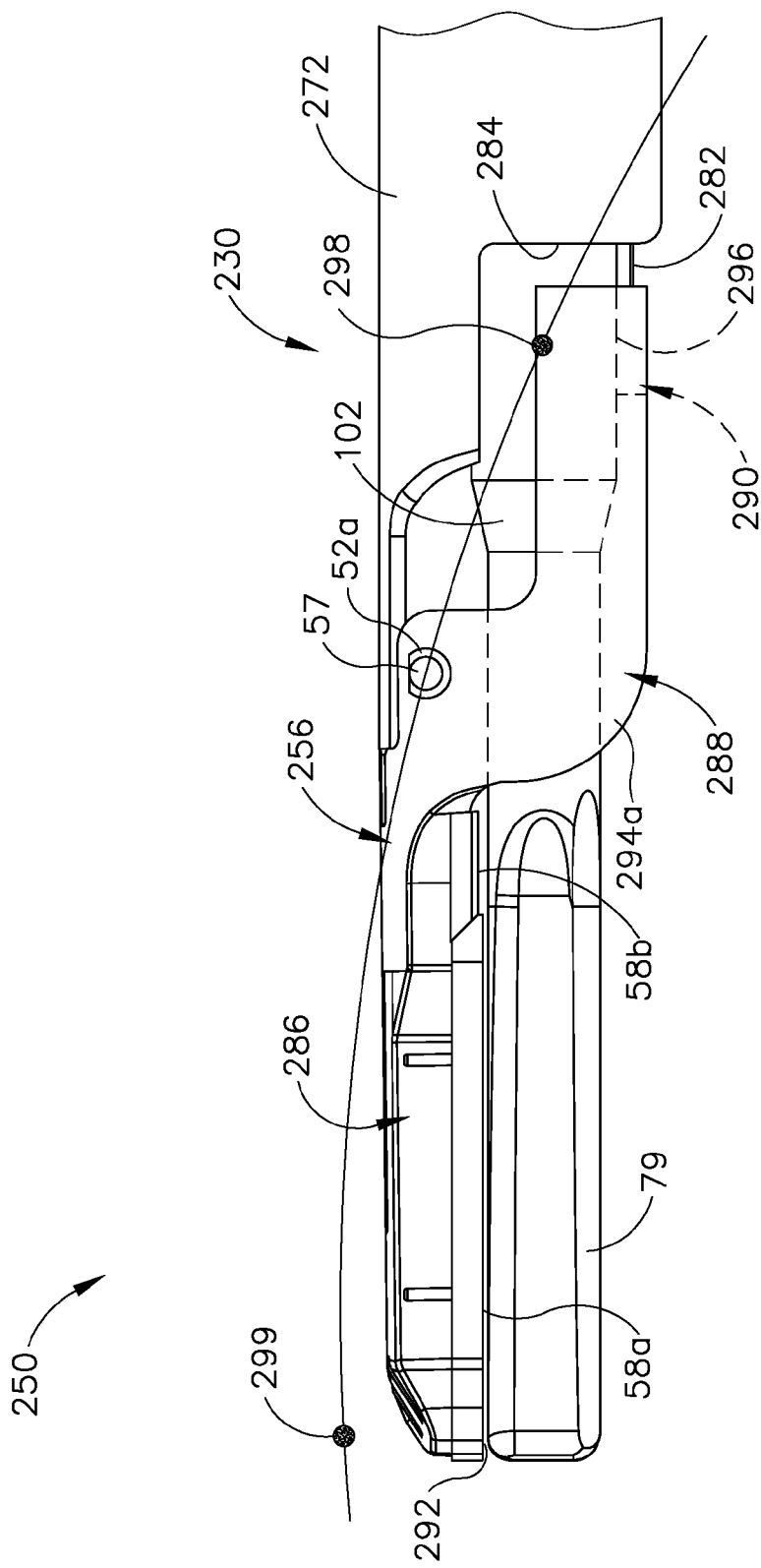
FIG. 9B depicts an enlarged side view of the end effector of FIG. 7 in the closed configuration.

In FIG. 9B, a wave is superimposed to represent the harmonic oscillation of waveguide (102) and blade (79), with a point (298) being identified at a position corresponding to a node associated with resonant ultrasonic vibrations communicated through the waveguide (102); and with another point (299) being identified at a position corresponding to an anti-node associated with resonant ultrasonic vibrations communicated through the waveguide (102). In this example, the distal end of the blade (79) is located at a position corresponding with the anti-node point (299). As also shown in FIG. 9B, the support members (294a, 294b) are configured to position the abutment (290) such that the abutment (290) engages the waveguide (102) at the node point (298). The abutment (290) thus receives little to no vibrations from the waveguide (102), which may prolong the useful life of the engagement clamp pad (296). It should be understood that clamp pad (296) is not located on a tissue affecting portion of clamp arm (256) or waveguide (102).

While the abutment (290) is supported by the support members (294a, 294b) for engagement with the waveguide (102), it will be appreciated that the abutment (290) may be alternatively positioned relative to the blade (79) to inhibit movement of the positive stop clamp arm (256). By way of example, any one of the clamp arm (256), the actuator (280), and the handle assembly (120) may include the abutment (290) in order to provide a positive stop for maintaining the gap (292), as shown in FIG. 9B. As such, it will be appreciated that the invention is not intended to be unnecessarily limited to the surgical instrument (200) shown and described herein.

In use, the clamp arm (256) is configured to move between the open and closed positions as respectively shown in FIGS. 9A-9B. In the open position, the push-pull cable assembly (282) directs the distal arm portion (286) to pivot upwardly away from the blade (79), while the proximal arm portion (288) simultaneously pivots downwardly away from the waveguide (102). The clamps pads (58a, 58b) and the blade (79) are thus open to receive the patient's tissue therebetween in order to begin clamping, sealing, and cutting the tissue.

Once tissue is suitably positioned between at least one clamp pad (58a, 58b) and blade (79), the user pivots trigger (128) toward pistol grip (124) to actuate the push-pull cable assembly (282) and pull the clamp arm (256) toward the blade (79). The distal arm portion (286) thus pivots downwardly to compress the tissue against the blade (79), while the proximal arm portion (288) simultaneously pivots upwardly toward waveguide (102). As shown in FIG. 9B, the clamp arm (256) continues to pivot until the engagement clamp pad (296) of the abutment (290) engages the waveguide (102) at the nodal position (298), thereby reaching the closed position. Notably, the clamp pads (58a, 58b) remain offset from the blade (79) and define the minimum gap (292) therebetween. In other words, the abutment (290) provides a positive stop for the clamp arm (256) for maintaining the minimum gap (292) and inhibiting the blade (79) from direct contact with each of the clamp pads (58a, 58b). Alternatively and as noted above, the design could be such as to allow the gap (292) to be zero, that is, the clamp pad or pads (58a or 58b) could fully close against the blade (79) and the function of the abutment (290) then is to limit wear of clamp pad or pads (58a or 58b) by reducing the rate at which clamp pads (58a or 58b) wear due to abutment (290) being fabricated from more robust materials than pad or pads (58a or 58b) and/or due to the abutment (290) engaging the blade (79) or waveguide (102) at a location of relatively low displacement.

V. Exemplary Surgical Instrument with Clamp Arm Alignment Features

In some instances, clamp arm (56, 144, 256) may undesirably deflect laterally relative to the longitudinal profile of ultrasonic blade (24, 79, 160). This may occur due to tolerance stacking between components and/or for various other reasons as will be apparent to those of ordinary skill in the art in view of the teachings herein. If clamp arm (56, 144, 256) laterally deflects at great enough angle, clamp pad (58a, 58b, 146) may not fully laterally align with ultrasonic blade (24, 79, 160) when end effector (50, 140, 250) is in a closed position (shown in FIGS. 3, 8B, 9B). Lateral misalignment between clamp arm (56, 144, 256) and ultrasonic blade (24, 79, 160) may lead to undesired effects such as insufficient tissue compression, which may further lead to improper cutting or sealing of tissue. Additionally, in some instances, the clamp arm (56, 144, 256) may not align rotationally to the ultrasonic blade (24, 79, 160) (i.e., about the longitudinal axis of blade (24, 79, 160)) which, again, may be due to tolerance stacking between components and/or for various other reasons as will be apparent to those of ordinary skill in the art in view of the teachings herein. Rotational misalignment between clamp arm (56, 144, 256) and ultrasonic blade (24, 79, 160), especially for end effectors that are curved, may lead to undesired effects such as insufficient tissue compression, which may further lead to improper cutting or sealing of tissue. It may therefore be desirable to provide a version of end effector (50, 140, 250) with guidance features that ensure proper lateral and rotational alignment of clamp arm (56, 144, 256) with clamp pad (58a, 58b, 146) when end effector (50, 140, 250) is in a closed configuration. Several merely illustrative examples of such features are described in greater detail below.

A. Aligning Features Associated with Clamp Arm and Ultrasonic Blade

FIGS. 10-14 show an exemplary end effector (350) attached to outer sheath (372) and inner tube (376). End effector (350), outer sheath (372), and inner tube (376) may be readily incorporated into instrument (20, 100, 200) described above. Outer sheath (372) and inner tube (376) are substantially similar to outer sheath (152, 272) and inner tube (134, 276) described above, except for the differences described below. Therefore it should be understood that inner tube (376) is slidably disposed within outer sheath (372). As such, inner tube (376) is operable to translate longitudinally within outer sheath (372) relative to outer sheath (372) to selectively open and close end effector (350). Any of the methods described above used to slide inner tube (376) relative to outer sheath (372) may be utilized.

Figure 10:
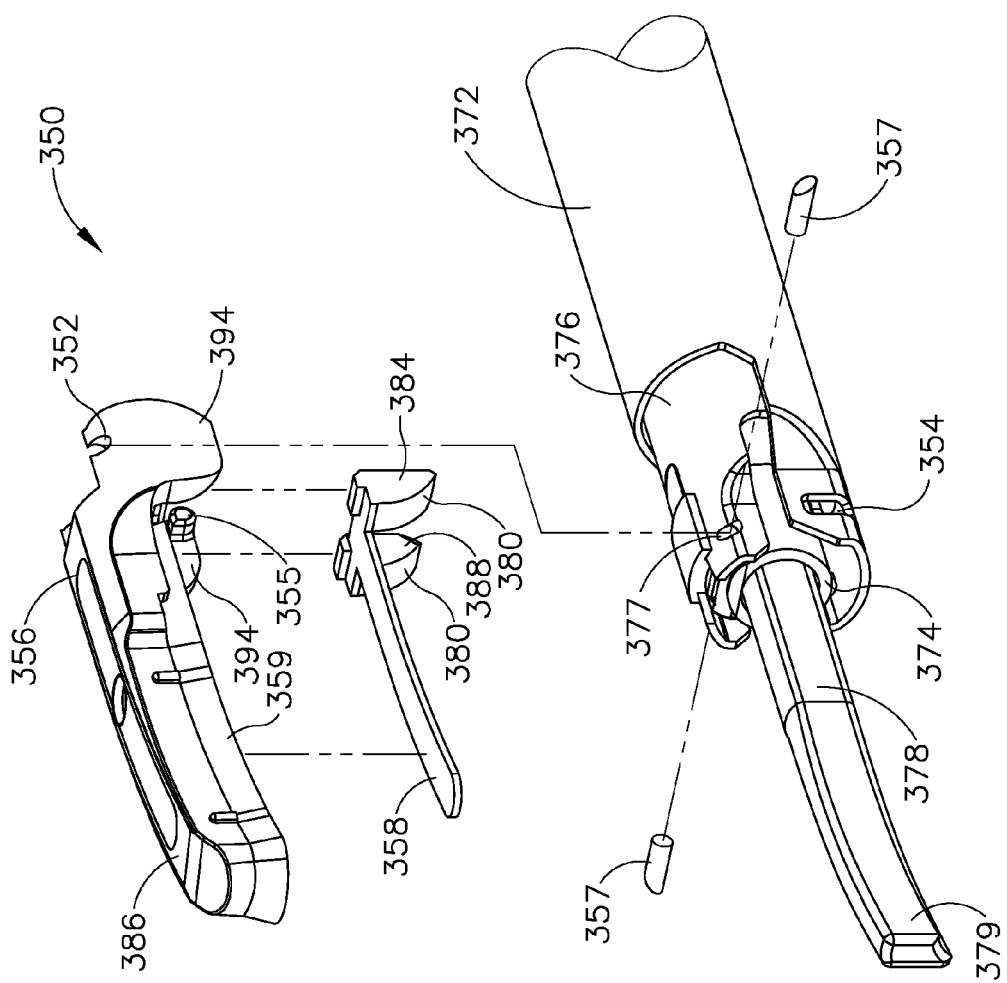
FIG. 10 depicts an exploded perspective view of another exemplary end effector that may be incorporated into the instrument of FIG. 2.
Figure 12A:
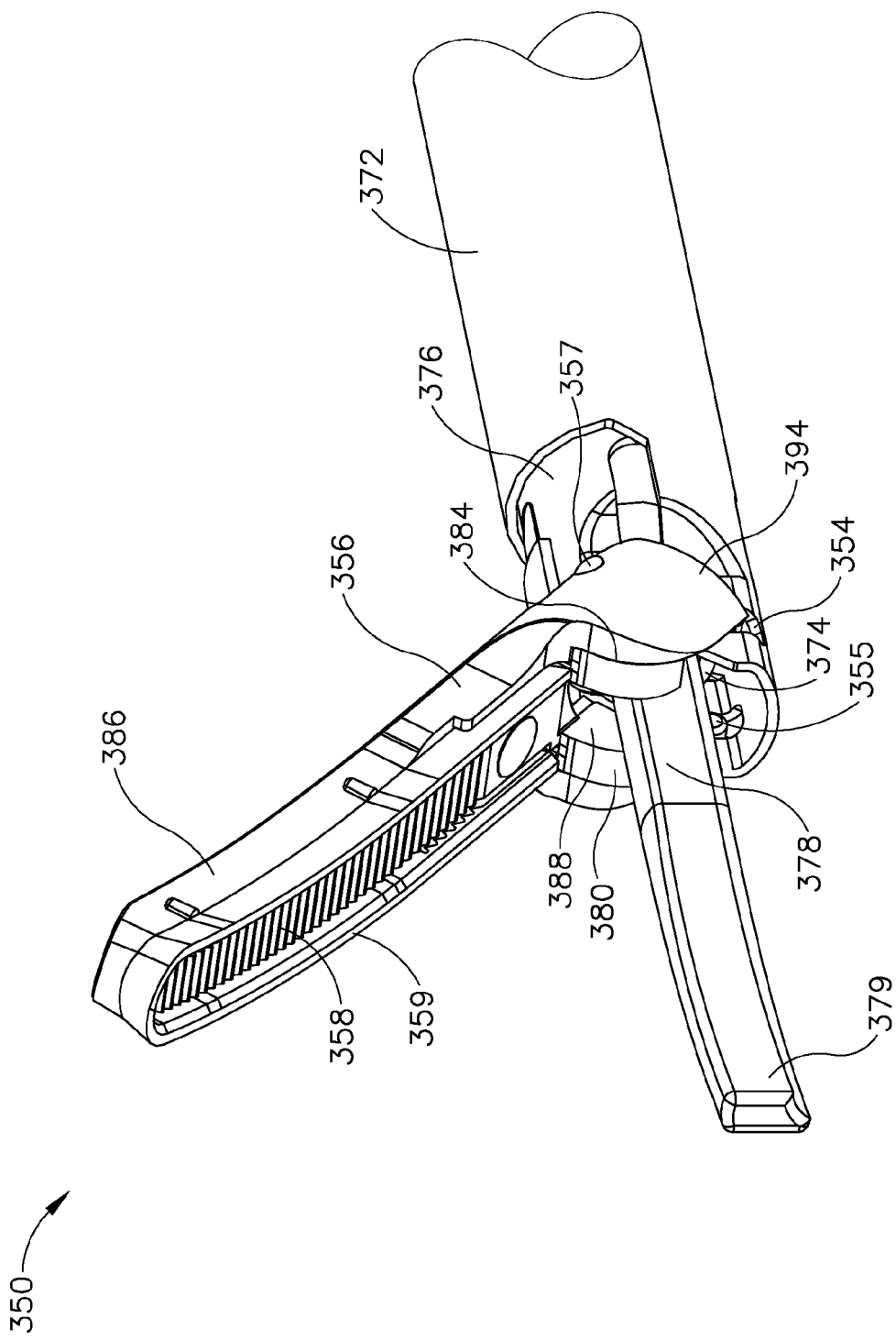
FIG. 12A depicts a perspective view of the end effector of FIG. 10 in an open configuration.
Figure 12B:
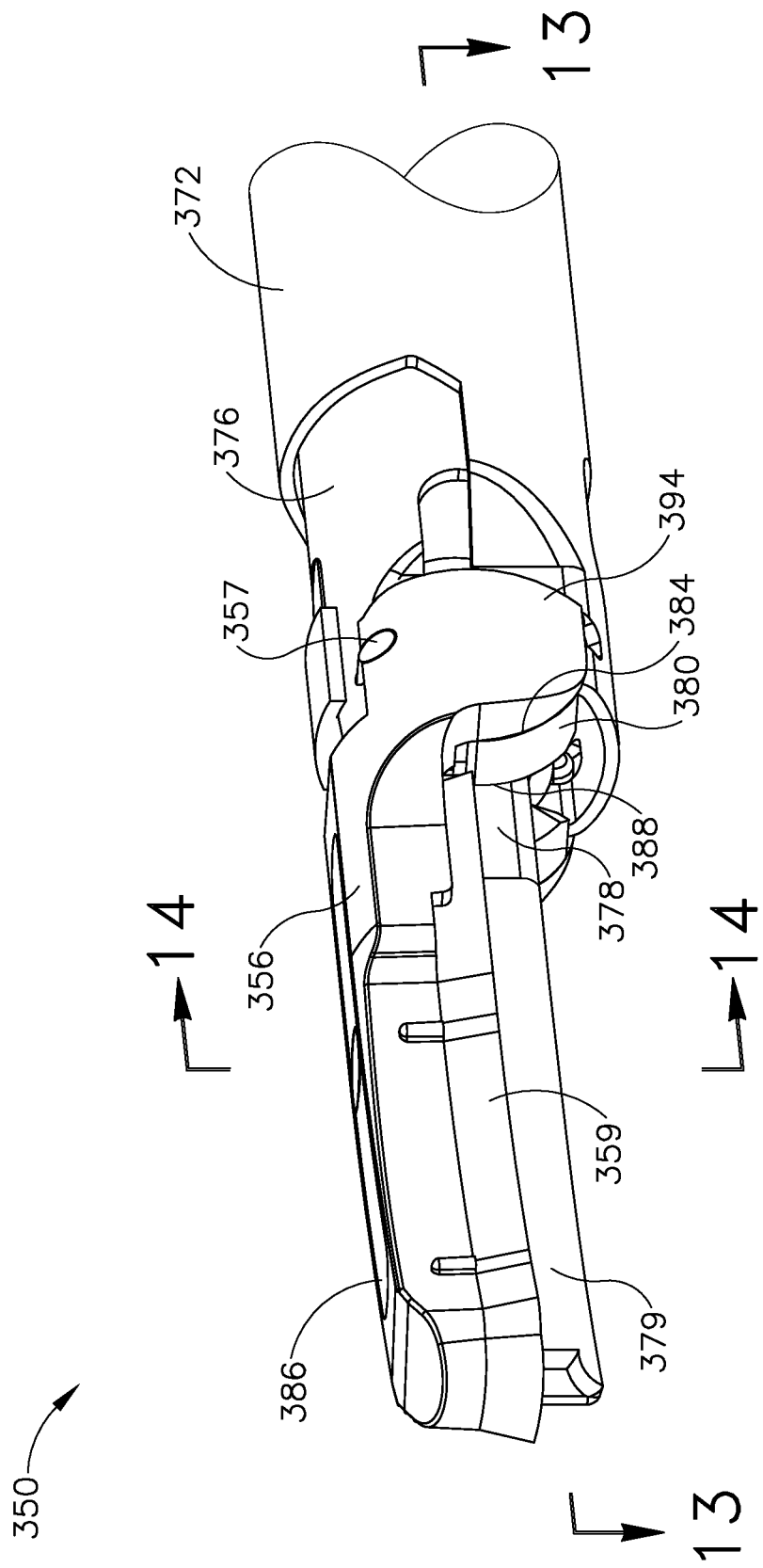
FIG. 12B depicts a perspective view of the end effector of FIG. 10 in a closed configuration.

End effector (350) includes a clamp arm (356), a clamp pad (358), and an ultrasonic blade (379). As best seen in FIG. 10, proximal end of ultrasonic blade (379) is covered by a blade sleeve (374). Blade sleeve (374) fixed relative to outer sheath (372) and extends within inner tube (376). Clamp arm (356) includes a pair of coupling holes (352), a pair of support members (394), integral studs (355) associated with each support member (395), and a distal arm portion (386). Clamp arm (356) is pivotally coupled to inner tube (376) via pivot pins (357). Pivot pins (357) may be inserted through coupling holes (352) of clamp arm (356) and openings (377) of inner tube (376). While in the current example two pivot pins (357) are utilized, it should be understood a single pivot pin (357) may be utilized to pivotally couple inner tube (376) and clamp arm (356). Integral studs (355) may be placed within openings (354) of outer sheath (372) to pivotably couple support members (394) with outer sheath (372). Therefore, as inner tube (376) translates relative to outer sheath (372), contact between integral studs (355) of clamp arm (356) and openings (354) of outer sheath (372) imparts a rotational force on clamp arm (356) about pivot pins (357). This may allow a user to selectively open and close clamp arm (356) relative to blade (379) as shown in FIGS. 12A-12B.

Clamp pad (358) is disposed within clamp arm (356). Clamp pad (358) may be substantially similar to clamp pad (146, 58a, 58b) described above, with differences described below. Clamp pad (358) includes a pair of downwardly extending guide features (380), each having a first mating surface (388) and a second mating surface (384). Guide features (380) are dimensioned such that each second mating surface (384) will contact the interior of support member (394) while clamp pad (358) is disposed within clamp arm (356). Contact between second mating surface (384) and interior of support member (394) may provide an interference fit such that clamp pad (358) is fixed relative to clamp arm (356). Therefore, it should be understood that clamp pad (358) rotates with clamp arm (356). Of course, any other method could be utilized to connect clamp pad (358) to clamp arm (356), such as any of the methods described above or any other method known to a person having ordinary skill in the art in view of the teachings herein.

By way of example only, clamp pad (358) may comprise a high temperature compatible, low wear, low friction material including polymers, elastomers, metals and ceramics or coated or filled versions thereof such as polytetrafluoroethylene, graphite-filled polytetrafluoroethylene, polyimide, fluorinated ethylene propylene, silicone, and/or any other suitable material (or combination of materials) as will be apparent to those of ordinary skill in the art in view of the teachings herein. By way of further example only, clamp pad (358) may further include fillers such as polytetrafluoroethylene, carbon, molybdenum disulfide, glass, metals (stainless, bronze, etc.), or calcium fluoride. By way of further example only, clamp pad (358) may further include one or more coatings such as FEP- or PTFE-based coatings. By way of further example only, clamp pad (358) may further comprise one or more ceramics such as alumina, zirconia, carbides, or nitrides. By way of further example only, clamp pad (358) may further comprise one or more polymers such as polyaryletherketone (PAEK) family of thermoplastics including PEEK, PEK, PEKK, PEEKK, PEKEKK and blends with other polymers such as PBI or fillers such as PTFE, graphite, carbon, molybdenum disulfide; polyimide and polyimide with fillers such as PTFE, graphite, carbon, molybdenum disulfide; PBI and PBI blended with other polymers; PTFE and PTFE with fillers such as graphite, carbon, molybdenum disulfide, glass, metalics (stainless, bronze, etc.), calcium fluoride; PPS; Polybenzimidazole-Polyetherketoneketone (PBI-PEKK); perfluoroalkoxy (PFA); glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos NanoTool. By way of further example only, clamp pad (358) may further include one or more elastomers such as silicones. Still other suitable materials that may be used to form clamp pad (358) will be apparent to those of ordinary skill in the art in view of the teachings herein.

Figure 11:
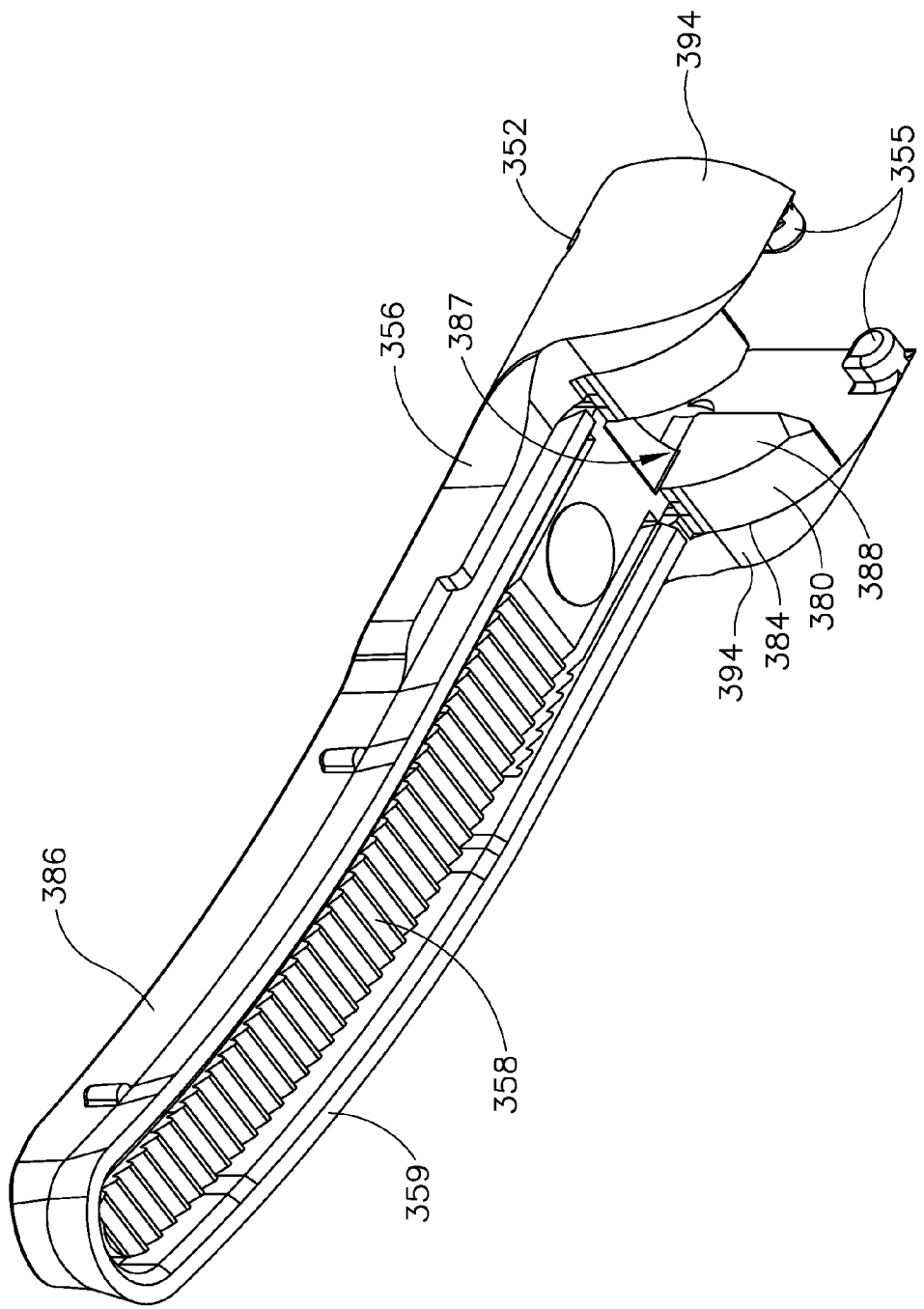
FIG. 11 depicts a perspective view of a clamp arm of end effector of FIG. 10.
Figure 13:
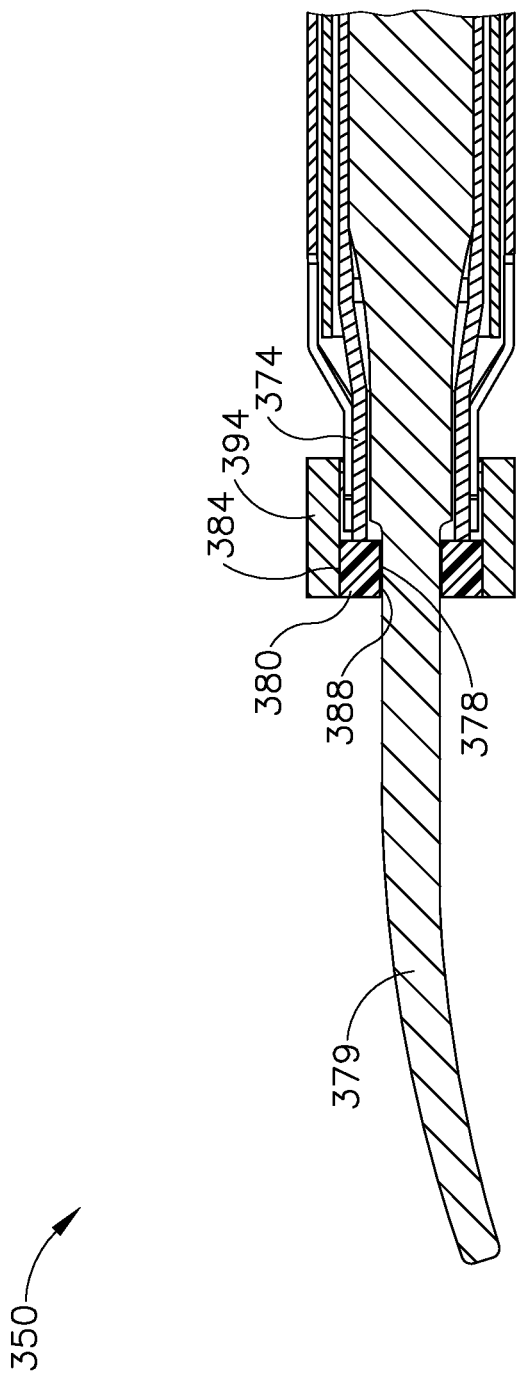
FIG. 13 depicts a cross-sectional view taken along line 13-13 of FIG. 12B.

As mentioned above, each guide feature (380) further includes first mating surface (388). As best seen in FIG. 11, first mating surfaces (388) of guide features (380) are dimensioned together to form a gap (387) that is sized and configured to receive blade (379). Blade (379) includes a pair of flats (378). As best seen in FIG. 13, guide features (380) are also dimensioned such that first mating surfaces (388) make contact with flats (378) when blade (379) is inserted through gap (387). As seen in FIGS. 12A-12B, contact between flats (378) of blade (379) and first mating surfaces (388) of guide features (380) may be continuous as end effector (350) transitions from an open position to a closed position. However, first mating surfaces (380) may also be dimensioned as to not contact flats (378) of blade (379) when end effector (350) is in an open position.

Contact between flats (378) of blade (379) and first mating surfaces (388) of guide features (380) may prevent clamp arm (356) from laterally deflecting relative to the longitudinal profile of blade (379). In other words, lateral positioning between clamp arm (356) and blade (379) may be more consistent due to contact between flats (378) and first mating surfaces, even in response to external forces imparted on end effector (350). This may allow for a narrower clamp arm (356) and/or clamp pad (358), as alignment between clamp pad (358) and clamp arm (356) may be more consistent. Additionally, contact between flats (378) of blade (379) and first mating surfaces (388) of guide features (380) may prevent clamp arm (356) from rotating about the longitudinal axis of blade (379). This may result in a more consistent distribution of forces imparted on tissue grasped by end effector (350). While the current example shows two flats (378) in contact with first mating surfaces (388) of two guide features (380), one guide features (380) and one flat (378) may also be utilized. In some versions, the gap between mating surfaces (388) of clamp pad (358) could initially be less than the width of the blade (379). As blade (379) is activated, the ultrasonic energy of blade (379) may displace the material of clamp pad (358), resulting in no/zero gap between the mating surfaces (388) of guide features (380) and the blade (379). The zero gap may provide minimal lateral and rotational misalignment between clamp pad (358) and blade (379).

Figure 14:
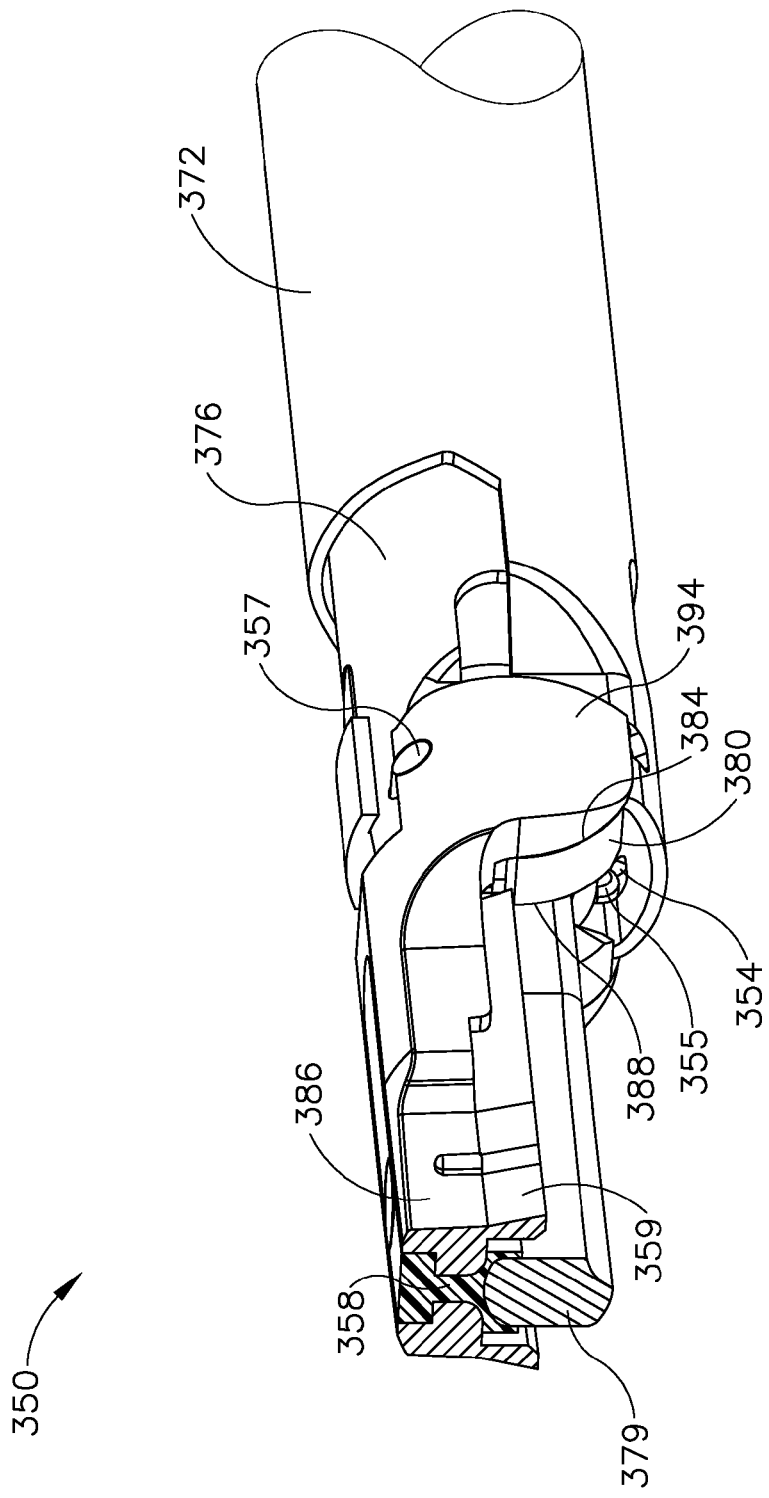
FIG. 14 depicts a cross-sectional perspective view taken along line 14-14 of FIG. 12B.

Additionally, end effector (350) could be configured to deliver electric energy to a surgical site through bipolar operation. Clamp arm (356) may thus be associated with one pole while an opposite pole may be associated with blade (379). Clamp pad (358) may thus act as an insulative material. As mentioned above, clamp pad (358) may encounter heat, compression forces, and vibrations generated via blade (379), which may work together to eventually wear out the material forming clamp pad (358). As best seen in FIG. 14, if contact between clamp pad (358) and blade (379) is more consistent, blade (379) may erode clamp pad (358) with a consistent lateral profile. If blade (379) erodes clamp pad (358) with a consistent lateral profile, the pole to pole distance between blade (379) and clamp arm (356) may remain relatively unchanged even after wearing of the material forming clamp pad (358).

End effector (350) may further be operable to apply bipolar RF electrosurgical energy to tissue. In particular, clamp arm (356) of the present example includes a skirt (359) that extends as a continuous part of the clamp arm (356) vertically toward blade (379). The vertical extent of skirt (359) is to about the level of the clamp pad (358) surface that engages tissue to slightly proud or recessed from this tissue engaging surface. Skirt (359) is located to the sides of clamp arm (356) and around the distal tip of clamp arm (356) and is distal to the distal termination of clamp pad (358). The portion of the skirt (359) at the tip of the clamp arm (356) may provide an advantage of being able to deliver bipolar coagulation RF energy to tissue that is distal to the clamped tissue, which is generally where a blind bite of tissue (i.e., where a conventional end effector does not fully span the target tissue) bleeds, especially in instances where a vessel is not fully captured in the clamp.

In some versions, guide features (380) are located along a position of blade (379) corresponding to a node associated with resonant ultrasonic vibrations communicated through blade (379). Thus, contact between flats (378) and first mating surfaces (388) may not be affected by oscillations of ultrasonic blade (379). In some other versions, guide features (380) are not located along a position of blade (379) corresponding to a node associated with resonant ultrasonic vibrations communicated through blade (379). In some such versions, guide features (380) are located along a position of blade (379) having low local blade (379) displacement such as locations with less than 50% of the tip displacement, or more particularly at locations having less than 30% of the tip displacement.

In addition to ensuring alignment in end effector (350), guide features (380) may also provide a positive tissue stop that may prevent tissue from traveling to a proximal region of end effector (350) where ultrasonic energy from blade (379) may not adequately sever or seal the tissue. In other words, guide features (380) may prevent the tissue from reach in a longitudinal region of blade that is too close to a node associated with resonant ultrasonic vibrations communicated through blade (379). Such a positive tissue stop may thus consistently and simply prevent tissue from inadvertently reaching a proximal position within end effector (350) where the tissue would be undesirably unaffected by blade (379). In providing such prevention, the positive tissue stop may eliminate the need for an operator to visualize proximal region of end effector (350) in order to determine whether the tissue has reached an undesirably proximal position within end effector (350).

While guide features (380) are shown largely distal to the clamp arm (356) pivot in the present example, where the pivot is located roughly concentric to the coupling holes (352), guide features (380) could alternatively be proximal to the clamp arm (356) pivot and could be, for example, incorporated into the abutment (290) of FIG. 9A-9B by adding vertical side walls which form geometry similar to guide features (380). As stated with abutment (290), guide features (380) may be located to engage blade (379) where the local blade displacement is less than 50% of the tip displacement of blade (379) and more particularly where the local displacement is less than 30% of the tip displacement of blade (379).

Figure 15:
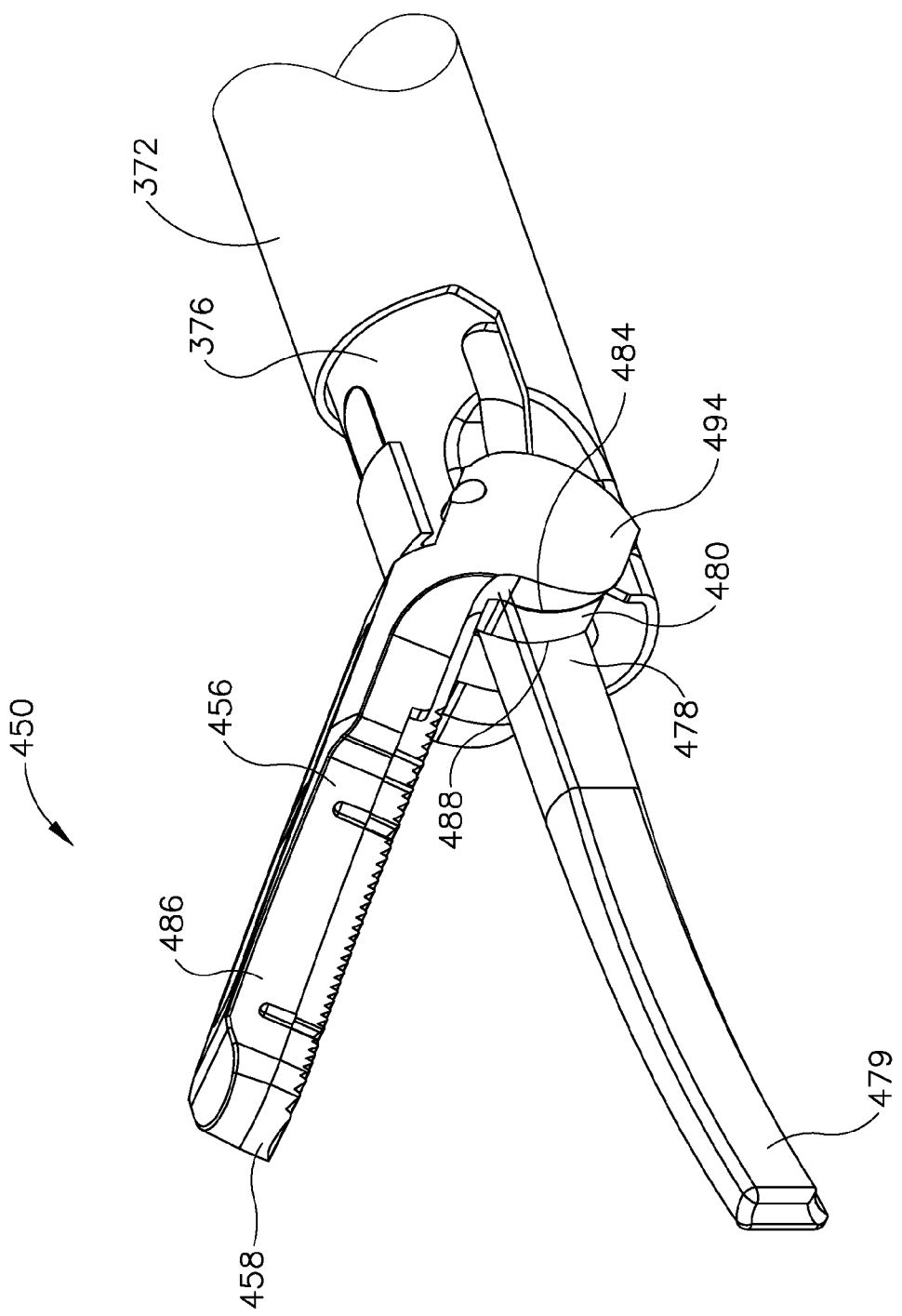
FIG. 15 depicts a perspective view of another exemplary end effector that may be incorporated into the instrument of FIG. 2.

FIG. 15 shows an alternative end effector (450) that may be readily incorporated into instrument (20, 100, 200) described above. End effector (450) includes a clamp arm (456) and an ultrasonic blade (479). Clamp arm (456) is substantially similar to clamp arm (356) referenced above. Clamp arm (456) thus connects to outer sheath (372) and inner tube (376) in a similar manner, and pivots from an open position to a closed position. Clamp arm (456) includes a distal arm portion (486), support members (494), and a clamp pad (458) having downwardly extending guide features (480). Each guide feature (480) includes a first mating surface (488) and a second mating surface (484). Distal arm portion (486), support members (494), clamp pad (458), guide features (480), first mating surface (488) and second mating surface (484) are substantially similar to distal arm portion (386), support members (394), clamp pad (358), guide features (380), first mating surface (388) and second mating surface (384) referenced above, respectively.

Blade (479) is substantially the same as blade (379) referenced above with differences described below. Instead of having flats (370), blade (479) of this example has a curved mating surface (478). Therefore, only a portion of first mating surface (488) makes contact with curved mating surface (478) of blade (479). However, contact between curved mating surface (478) and first mating surface (488) still may prevent clamp arm (456) from laterally deflecting relative to the longitudinal axis of blade (379). This alignment may lead to similar benefits described above for end effector (350). Additionally, contact between curved mating surface (478) of blade (479) and first mating surfaces (488) of guide features (480) may prevent clamp arm (456) from rotating about the longitudinal axis of blade (479). This alignment may lead to similar benefits described above for end effector (350). It should also be understood that the contact between tapered mating surfaces (488) and blade (479) may occur at a longitudinal position corresponding to a node associated with resonant ultrasonic vibrations communicated through blade (479).

In addition to ensuring alignment in end effector (450), guide features (480) may also provide a positive tissue stop that may prevent tissue from traveling to a proximal region of end effector (450) where ultrasonic energy from blade (479) may not adequately sever or seal the tissue. In other words, guide features (380) may prevent the tissue from reach in a longitudinal region of blade that is too close to a node associated with resonant ultrasonic vibrations communicated through blade (479). Such a positive tissue stop may thus consistently and simply prevent tissue from inadvertently reaching a proximal position within end effector (450) where the tissue would be undesirably unaffected by blade (479). In providing such prevention, the positive tissue stop may eliminate the need for an operator to visualize proximal region of end effector (450) in order to determine whether the tissue has reached an undesirably proximal position within end effector (450).

Figure 16:
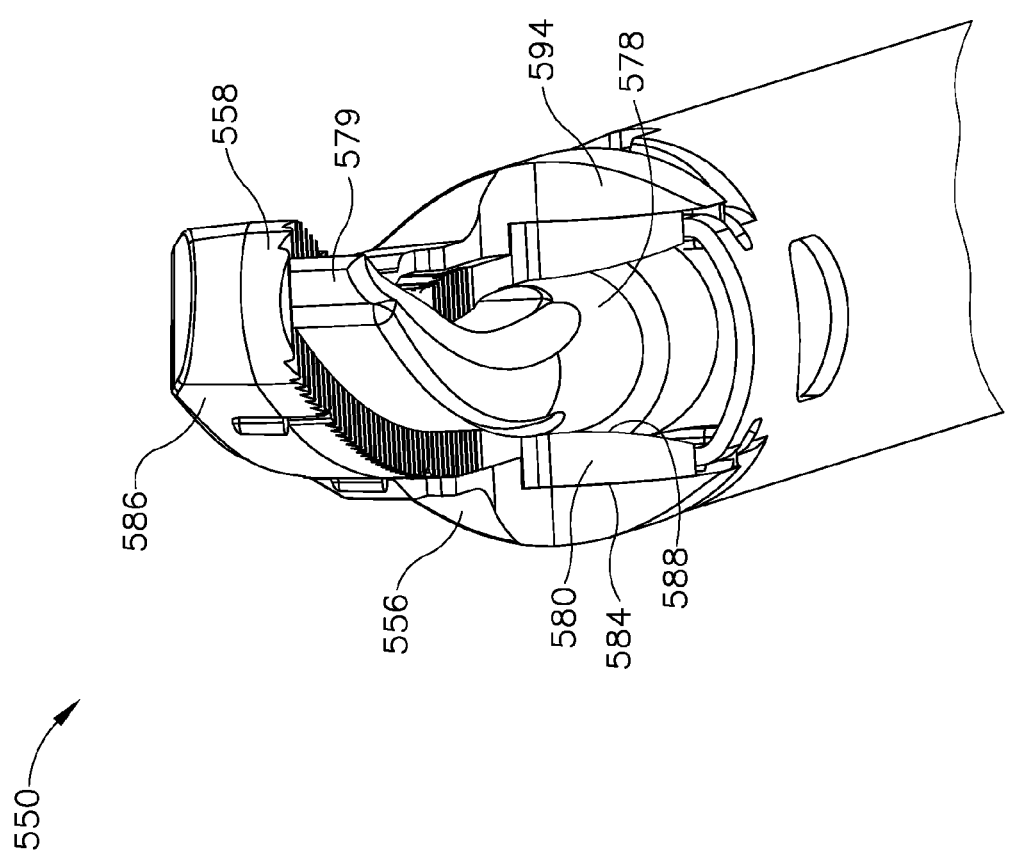
FIG. 16 depicts a perspective view of another exemplary end effector that may be incorporated into the instrument of FIG. 2.

FIG. 16 shows an alternative end effector (550) that may be readily incorporated into instrument (20, 100, 200) described above. End effector (550) includes a clamp arm (556) and an ultrasonic blade (579). Clamp arm (556) is substantially similar to clamp arm (356) referenced above, with the differences described below. Clamp arm (556) thus connects to outer sheath (372) and inner tube (376) in a similar manner, and pivots from an open position to a closed position. Clamp arm (556) includes a distal arm portion (586), support members (594), and a clamp pad (558) having downwardly extending guide features (580).

By way of example only, clamp pad (558) may comprise a high temperature compatible, low wear, low friction material including polymers, elastomers, metals and ceramics or coated or filled versions thereof such as polytetrafluoroethylene, graphite-filled polytetrafluoroethylene, polyimide, fluorinated ethylene propylene, silicone, and/or any other suitable material (or combination of materials) as will be apparent to those of ordinary skill in the art in view of the teachings herein. By way of further example only, clamp pad (558) may further include fillers such as polytetrafluoroethylene, carbon, molybdenum disulfide, glass, metals (stainless, bronze, etc.), or calcium fluoride. By way of further example only, clamp pad (558) may further include one or more coatings such as FEP- or PTFE-based coatings. By way of further example only, clamp pad (558) may further comprise one or more ceramics such as alumina, zirconia, carbides, or nitrides. By way of further example only, clamp pad (558) may further comprise one or more polymers such as polyaryletherketone (PAEK) family of thermoplastics including PEEK, PEK, PEKK, PEEKK, PEKEKK and blends with other polymers such as PBI or fillers such as PTFE, graphite, carbon, molybdenum disulfide; polyimide and polyimide with fillers such as PTFE, graphite, carbon, molybdenum disulfide; PBI and PBI blended with other polymers; PTFE and PTFE with fillers such as graphite, carbon, molybdenum disulfide, glass, metalics (stainless, bronze, etc.), calcium fluoride; PPS; Polybenzimidazole-Polyetherketoneketone (PBI-PEKK); perfluoroalkoxy (PFA); glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos NanoTool. By way of further example only, clamp pad (558) may further include one or more elastomers such as silicones. Still other suitable materials that may be used to form clamp pad (558) will be apparent to those of ordinary skill in the art in view of the teachings herein.

Each guide feature (580) includes a first tapered mating surface (588) and a second mating surface (584). Distal arm portion (586), support members (594), clamp pad (558), guide features (580), and second mating surface (584) are substantially similar to distal arm portion (386), support members (394), clamp pad (358), guide features (380), first mating surface (388) and second mating surface (384) referenced above, respectively. Blade (579) is substantially the same as blade (479) referenced above, having a curved mating surface (578).

As mentioned above, each guide feature (580) includes a first tapered mating surface (588), instead of flat mating surfaces discussed above. Tapered mating surface (588) may allow guide features (580) of clamp pad (558) to engage blade (579) while end effector (550) is in a closed position. However, tapered mating surface (588) may not allow guide features (580) of clamp pad (558) to engage blade (579) while end effector (550) is in an open position. Therefore, as clamp arm (556) pivots toward blade (579), contact between curved mating surface (578) and tapered mating surface (588) may still prevent clamp arm (556) from laterally deflecting relative to the longitudinal axis of blade (579) when end effector (550) is in a closed position. This alignment may lead to similar benefits described above for end effector (350). Additionally, contact between curved mating surface (578) of blade (579) and tapered mating surfaces (588) of guide features (580) may prevent clamp arm (556) from rotating about the longitudinal axis of blade (579) when end effector (550) is in a closed position. This alignment may lead to similar benefits described above for end effector (350).

While in the current example, end effector (550) utilizes blade (579) having a curved mating surface (578), it should be understood blade (579) may also incorporate flats similar to flats (378) described above. It should also be understood that the contact between tapered mating surfaces (588) and blade (579) may occur at a longitudinal position corresponding to a node associated with resonant ultrasonic vibrations communicated through blade (579).

In addition to ensuring alignment in end effector (550), guide features (580) may also provide a positive tissue stop that may prevent tissue from traveling to a proximal region of end effector (550) where ultrasonic energy from blade (579) may not adequately sever or seal the tissue. In other words, guide features (580) may prevent the tissue from reach in a longitudinal region of blade that is too close to a node associated with resonant ultrasonic vibrations communicated through blade (579). Such a positive tissue stop may thus consistently and simply prevent tissue from inadvertently reaching a proximal position within end effector (550) where the tissue would be undesirably unaffected by blade (579). In providing such prevention, the positive tissue stop may eliminate the need for an operator to visualize proximal region of end effector (550) in order to determine whether the tissue has reached an undesirably proximal position within end effector (550).

Figure 17A:
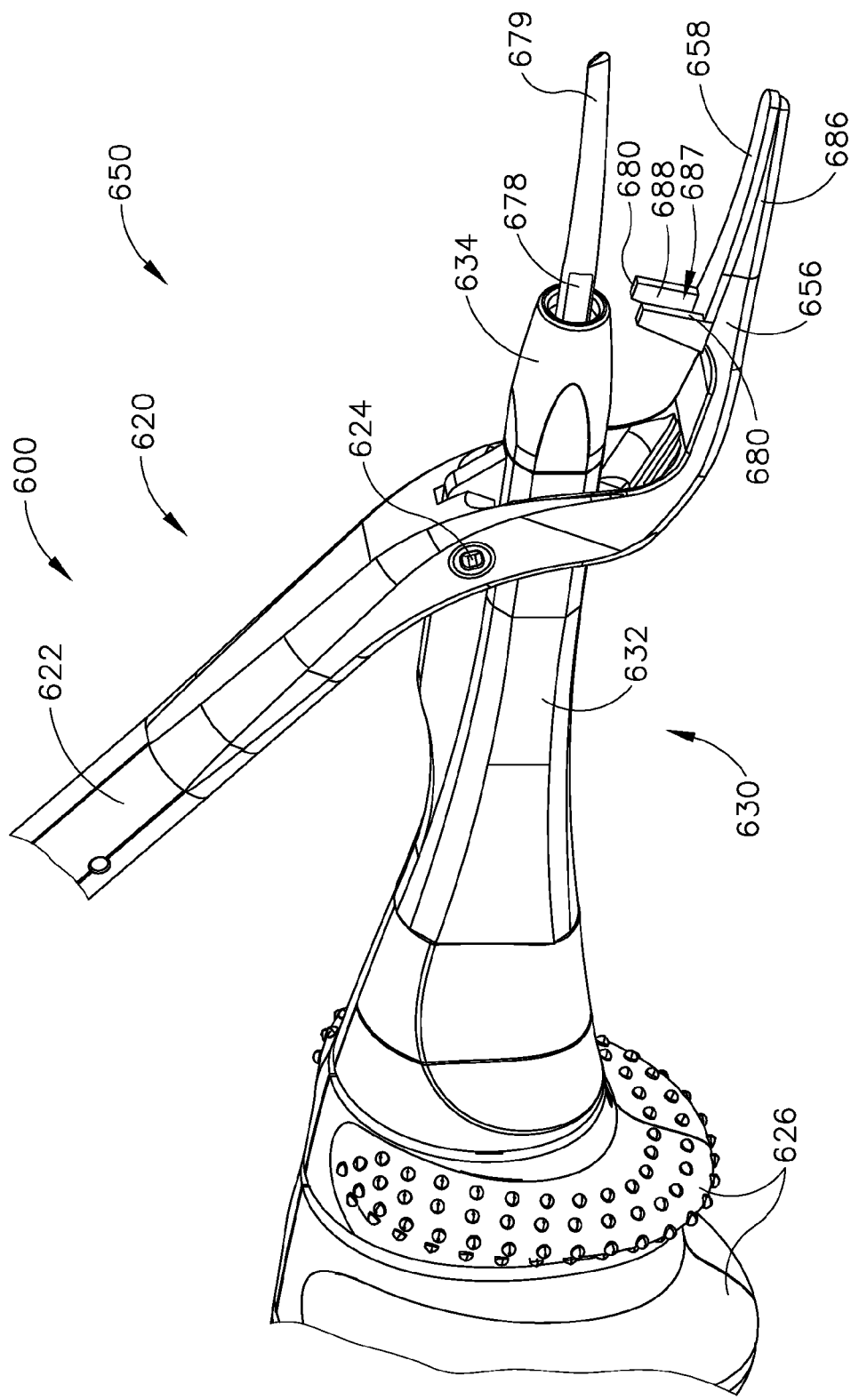
FIG. 17A depicts a perspective view of another exemplary surgical instrument that may be incorporated into the system of FIG. 1, with the instrument in a first configuration.
Figure 17B:
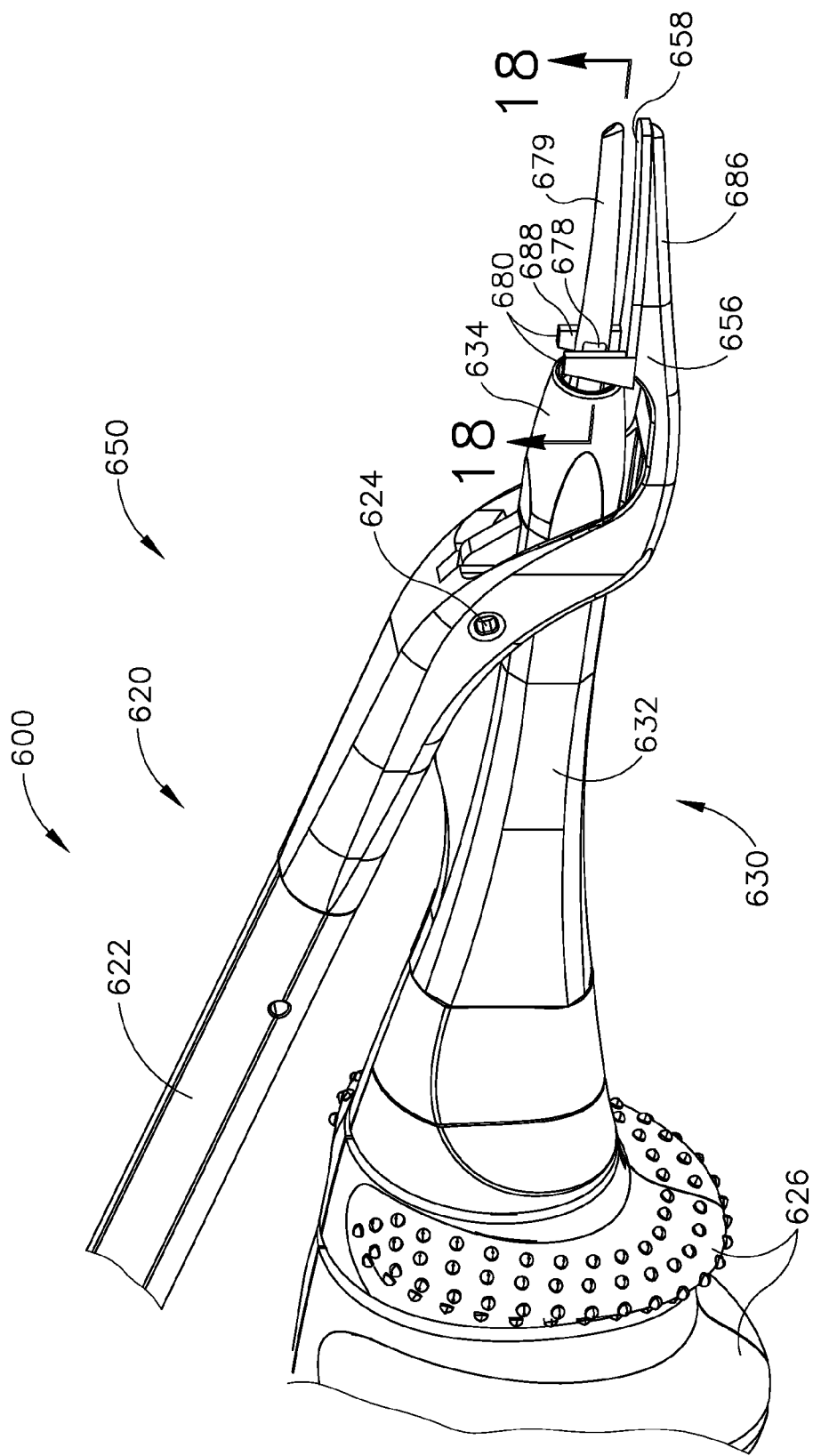
FIG. 17B depicts a perspective view of the surgical instrument of FIG. 17A in a second configuration.

FIGS. 17A-17B illustrate an exemplary ultrasonic surgical instrument (600) that is configured to be used in open surgical procedures. Instrument (600) of this example comprises a handle assembly (610), a shaft assembly (630), and an end effector (650). Handle assembly (610) may include a body (612) including a finger grip ring (not shown) and a pair of buttons (626). Instrument (600) also includes a clamp arm assembly (620) that is pivotable toward and away from body (612). Clamp arm assembly (620) includes a shank (622) with a thumb grip ring (not shown). Thumb grip ring (not shown) and finger grip ring (not shown) together provide a scissor grip type of configuration. It should be understood, however, that various other suitable configurations may be used, including but not limited to a pistol grip configuration.

Shaft assembly (630) comprises an outer sheath (632) extending distally from body (612). A cap (634) is secured to the distal end of sheath (632). End effector (650) comprises an ultrasonic blade (679) and a clamp arm (656). Ultrasonic blade (679) extends distally from cap (634). Clamp arm (656) is an integral feature of clamp arm assembly (620). Clamp arm (656) includes a clamp pad (658) facing ultrasonic blade (679). Clamp arm assembly (620) is pivotally coupled with outer sheath (632) via a pin (624). Clamp arm (656) is positioned distal to pin (624); while shank (622) and thumb grip ring (not shown) are positioned proximal to pin (624). Thus clamp arm (656) is pivotable toward and away from ultrasonic blade (679) based on pivoting of thumb grip ring (not shown) toward and away from body (612) of handle assembly (610). It should therefore be understood that an operator may squeeze thumb grip ring (not shown) toward body (612) to thereby clamp tissue between clamp pad (658) and ultrasonic blade (679) to transect and/or seal the tissue. In some versions, one or more resilient members are used to bias clamp arm (656) to the open position shown in FIG. 17A. By way of example only, such a resilient member may comprise a leaf spring, a torsion spring, and/or any other suitable kind of resilient member.

Figure 18:
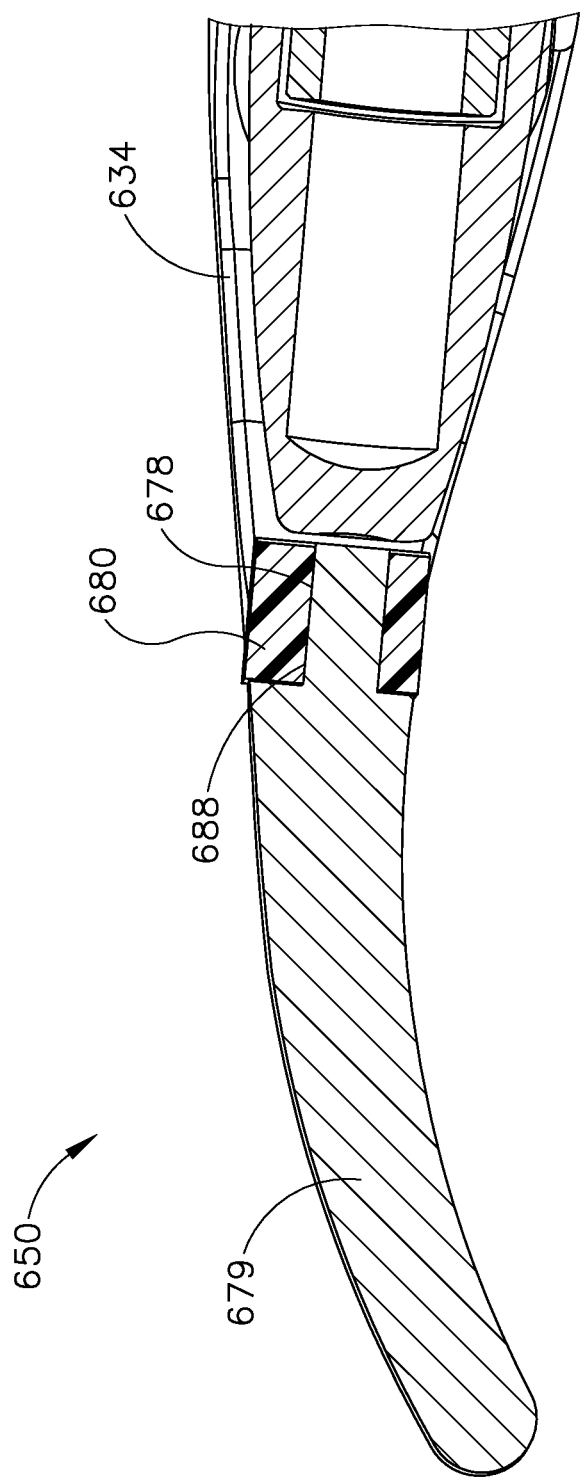
FIG. 18 depicts a cross-sectional view of the surgical instrument of FIG. 17A taken along line 18-18 of FIG. 17B.

Additionally, clamp pad (658) further includes a pair of guide features (680), each having a first mating surface (688). As best seen in FIG. 17A, first mating surfaces (688) of guide features (680) are dimensioned together to form a gap (687) that is sized and configured to receive blade (679). Blade (679) includes a pair of flats (678). As best seen in FIG. 18, guide feature (680) is also dimensioned such that first mating surfaces (688) make contact with flats (678) when blade (679) rotates through gap (687). By way of example only, clamp pad (658) may comprise a high temperature compatible, low wear, low friction material including polymers, elastomers, metals and ceramics or coated or filled versions thereof such as polytetrafluoroethylene, graphite-filled polytetrafluoroethylene, polyimide, fluorinated ethylene propylene, silicone, and/or any other suitable material (or combination of materials) as will be apparent to those of ordinary skill in the art in view of the teachings herein. By way of further example only, clamp pad (658) may further include fillers such as polytetrafluoroethylene, carbon, molybdenum disulfide, glass, metals (stainless, bronze, etc.), or calcium fluoride.

By way of further example only, clamp pad (658) may further include one or more coatings such as FEP- or PTFE-based coatings. By way of further example only, clamp pad (658) may further comprise one or more ceramics such as alumina, zirconia, carbides, or nitrides. By way of further example only, clamp pad (658) may further comprise one or more polymers such as polyaryletherketone (PAEK) family of thermoplastics including PEEK, PEK, PEKK, PEEKK, PEKEKK and blends with other polymers such as PBI or fillers such as PTFE, graphite, carbon, molybdenum disulfide; polyimide and polyimide with fillers such as PTFE, graphite, carbon, molybdenum disulfide; PBI and PBI blended with other polymers; PTFE and PTFE with fillers such as graphite, carbon, molybdenum disulfide, glass, metalics (stainless, bronze, etc.), calcium fluoride; PPS; Polybenzimidazole-Polyetherketoneketone (PBI-PEKK); perfluoroalkoxy (PFA); glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos NanoTool. By way of further example only, clamp pad (658) may further include one or more elastomers such as silicones. Still other suitable materials that may be used to form clamp pad (658) will be apparent to those of ordinary skill in the art in view of the teachings herein.

Contact between flats (678) of blade (679) and first mating surfaces (688) of guide features (680) may prevent clamp arm (656) from laterally deflecting relative to the longitudinal axis of blade (679). In other words, lateral positioning between clamp arm (656) and blade (679) may be more consistent due to contact between flats (678) and first mating surfaces (688), even in response to external forces imparted on end effector (650). This may allow for a narrower clamp arm (656) and/or clamp pad (658), as alignment between clamp pad (658) and clamp arm (656) may be more consistent. Additionally, contact between flats (678) of blade (679) and first mating surfaces (688) of guide features (680) may prevent clamp arm (656) from rotating about the longitudinal axis of blade (679). This may result in a more consistent distribution of forces imparted on tissue grasped by end effector (650). While the current example shows two flats (678) in contact with first mating surfaces (688) of two guide features (680), one guide features (680) and one flat (678) may also be utilized. It should also be understood that the contact between mating surfaces (688) and blade (679) may occur at a longitudinal position corresponding to a node associated with resonant ultrasonic vibrations communicated through blade (679). The opening of end effector (650) may be limited by methods that will become clear to those skilled in the art in view of this material. The limiting of the opening of end effector (650) may be such that at maximum tip aperture, the maximum distance between the distal tip of ultrasonic blade (679) and the distal tip of clamp pad (658), guide feature (680) remains engaged, or overlap vertically, flats (678) on blade (679) so that a transition from guided to unguided or vice versa is not felt by the operator when closing or opening end effector (650)

In addition to ensuring alignment in end effector (650), guide features (680) may also provide a positive tissue stop that may prevent tissue from traveling to a proximal region of end effector (650) where ultrasonic energy from blade (679) may not adequately sever or seal the tissue. In other words, guide features (680) may prevent the tissue from reach in a longitudinal region of blade that is too close to a node associated with resonant ultrasonic vibrations communicated through blade (679). Such a positive tissue stop may thus consistently and simply prevent tissue from inadvertently reaching a proximal position within end effector (650) where the tissue would be undesirably unaffected by blade (679). In providing such prevention, the positive tissue stop may eliminate the need for an operator to visualize proximal region of end effector (650) in order to determine whether the tissue has reached an undesirably proximal position within end effector (650).

Figure 19:
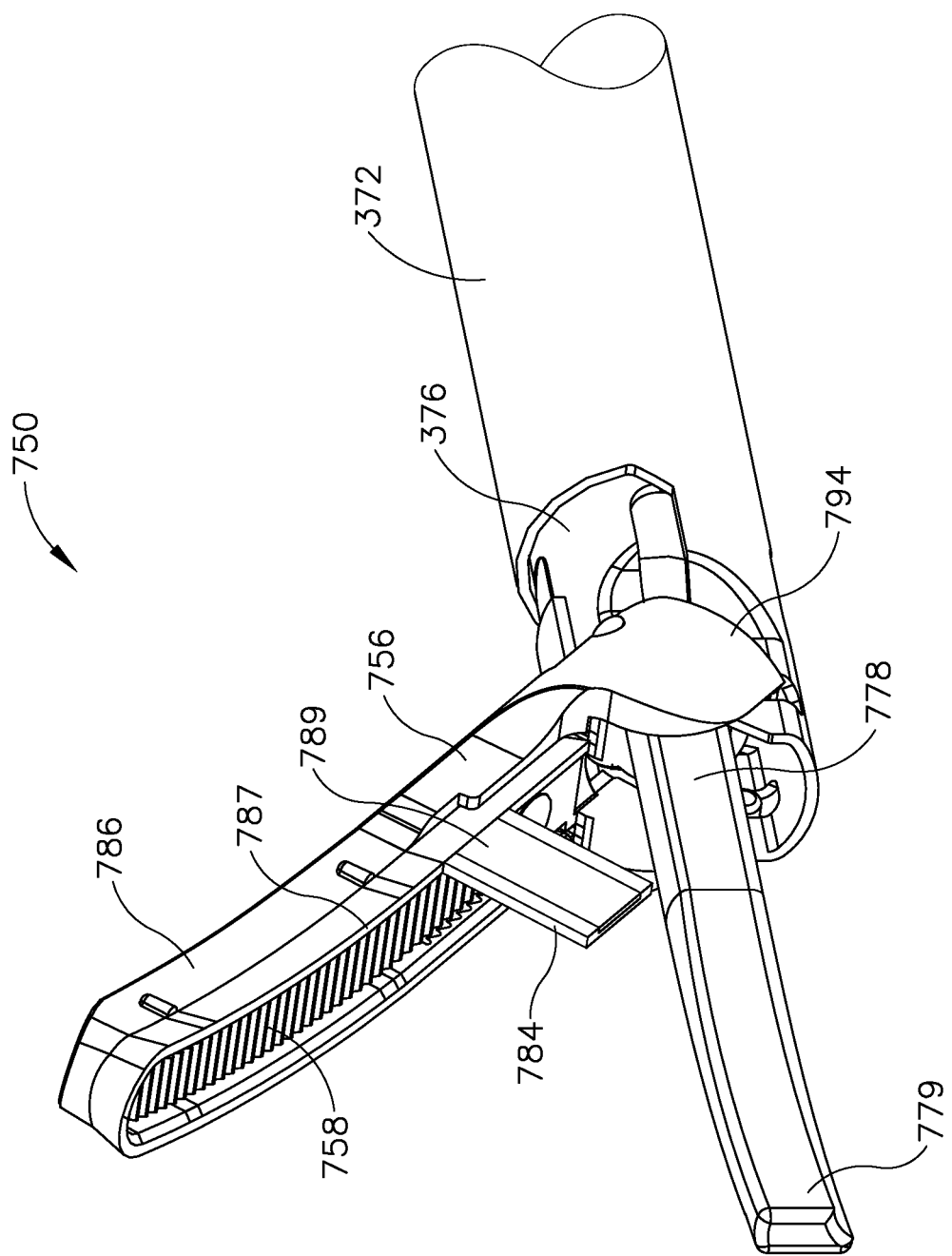
FIG. 19 depicts a perspective view of another exemplary end effector that may be incorporated into the instrument of FIG. 2, with the end effector in an open configuration.

FIG. 19 shows an exemplary end effector (750) attached to outer sheath (372) and inner tube (376). End effector (750), outer sheath (372), and inner tube (376) may be readily incorporated into instrument (20, 100, 200) described above. Therefore it should be understood that inner tube (376) is slidably disposed within outer sheath (372) Inner tube (376) is thus operable to translate longitudinally within outer sheath (372) relative to outer sheath (372) to selectively open and close end effector (750). Any of the methods described above used to slide inner tube (376) relative to outer sheath (372) may be utilized.

End effector (750) includes clamp arm (756) and ultrasonic blade (779). Ultrasonic blade (779) is substantially similar to ultrasonic blade (379) described above. Therefore, ultrasonic blade (779) includes a flat mating surface (778). Clamp arm (756) is substantially similar to clamp arm (356) referenced above, with differences described below. Clamp arm (756) includes a pair of support members (794), a distal arm member (786), a clamp pad (758), a lip (787) surrounding clamp pad (758), and a protrusion (789) extending downwardly from lip (787) toward flat mating surface (778) of blade (779). Protrusion (789) also includes pad material (784), which is configured to contact flat mating surface (778) as will be described below.

Clamp pad (758) may be substantially similar to clamp pad (58a, 58b, 146) described above. By way of example only, clamp pad (758) may comprise a high temperature compatible, low wear, low friction material including polymers, elastomers, metals and ceramics or coated or filled versions thereof such as polytetrafluoroethylene, graphite-filled polytetrafluoroethylene, polyimide, fluorinated ethylene propylene, silicone, and/or any other suitable material (or combination of materials) as will be apparent to those of ordinary skill in the art in view of the teachings herein. By way of further example only, clamp pad (758) may further include fillers such as polytetrafluoroethylene, carbon, molybdenum disulfide, glass, metals (stainless, bronze, etc.), or calcium fluoride. By way of further example only, clamp pad (758) may further include one or more coatings such as FEP- or PTFE-based coatings. By way of further example only, clamp pad (758) may further comprise one or more ceramics such as alumina, zirconia, carbides, or nitrides. By way of further example only, clamp pad (758) may further comprise one or more polymers such as polyaryletherketone (PAEK) family of thermoplastics including PEEK, PEK, PEKK, PEEKK, PEKEKK and blends with other polymers such as PBI or fillers such as PTFE, graphite, carbon, molybdenum disulfide; polyimide and polyimide with fillers such as PTFE, graphite, carbon, molybdenum disulfide; PBI and PBI blended with other polymers; PTFE and PTFE with fillers such as graphite, carbon, molybdenum disulfide, glass, metalics (stainless, bronze, etc.), calcium fluoride; PPS; Polybenzimidazole-Polyetherketoneketone (PBI-PEKK); perfluoroalkoxy (PFA); glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos NanoTool. By way of further example only, clamp pad (758) may further include one or more elastomers such as silicones. Still other suitable materials that may be used to form clamp pad (758) will be apparent to those of ordinary skill in the art in view of the teachings herein.

It should be understood that clamp pad (758) does not included guide features in contact with support member (794) and flat mating surface (778). Instead, protrusion (789) covered in pad material (784) is configured to contact flat mating surface (778) of blade (779) when end effector (750) is in a closed position. More specifically, pad material (784) is configured to contact flat mating surface (778) of blade (779) while protrusion (789) provides the structural support to maintain alignment between clamp arm (756) and blade (779). Therefore, clamp pad (758) itself does not help laterally and rotationally align clamp arm (756) with blade (779), but protrusion (789) and pad material (784) help align clamp arm (756) with blade (779).

Contact between flat (778) of blade (779) and pad material (784) of protrusion (789) may prevent clamp arm (756) from laterally deflecting relative to the longitudinal axis of blade (779). In other words, lateral positioning between clamp arm (756) and blade (779) may be more consistent due to the contact between flat (778) and pad material (784), even in response to external forces imparted on end effector (750). This may allow for a narrower clamp arm (756) and/or clamp pad (758), as alignment between clamp pad (758) and clamp arm (756) may be more consistent. Additionally, contact between flat (778) of blade (779) and pad material (784) of protrusion (789) may prevent clamp arm (756) from rotating about the longitudinal axis of blade (779). This may result in a more consistent distribution of forces imparted on tissue grasped by end effector (750). While the current example shows one protrusion (789) covered in pad material (784) in contact with flat (778), it is envisioned that two flats (778) on opposite sides of blade (779) may be in contact with two separate protrusions (789) covered in pad material (784). It should also be understood that the contact between pad material (784) and blade (779) may occur at a longitudinal position corresponding to a node associated with resonant ultrasonic vibrations communicated through blade (779).

In addition to ensuring alignment in end effector (750), protrusion (789) may also provide a positive tissue stop that may prevent tissue from traveling to a proximal region of end effector (750) where ultrasonic energy from blade (779) may not adequately sever or seal the tissue. In other words, protrusion (789) may prevent the tissue from reach in a longitudinal region of blade that is too close to a node associated with resonant ultrasonic vibrations communicated through blade (779). Such a positive tissue stop may thus consistently and simply prevent tissue from inadvertently reaching a proximal position within end effector (750) where the tissue would be undesirably unaffected by blade (779). In providing such prevention, the positive tissue stop may eliminate the need for an operator to visualize proximal region of end effector (750) in order to determine whether the tissue has reached an undesirably proximal position within end effector (750).

B. Alignment Features Associated with Clamp Arm and Blade Sleeve

FIGS. 20A-22 show an exemplary end effector (850) attached to outer sheath (372) and inner tube (376). End effector (850), outer sheath (372) and inner tube (376) may be readily incorporated into instrument (20, 100, 200) described above. Therefore it should be understood that inner tube (376) is slidably disposed within outer sheath (372). Inner tube (376) is thus operable to translate longitudinally within outer sheath (372) relative to outer sheath (372) to selectively open and close end effector (850). Any of the methods described above used to slide inner tube (376) relative to outer sheath (372) may be utilized.

End effector (850) includes a clamp arm (856), a clamp pad (858) housed within clamp arm (856), an ultrasonic blade (879), and an extended blade sleeve (874) partially housing ultrasonic blade (879). It should be understood that extended blade sleeve (874) is similar to blade sleeve (374) in the fact extended blade sleeve (874) is fixed relative to outer sheath (372) and extends within inner tube (376). Extended blade sleeve (874) is also fixed relative to ultrasonic blade (879). Extended blade sleeve (874) also includes a pair of upwardly extending protrusions (875). As will be described in greater detail below, protrusions (875) help align clamp arm (856) with ultrasonic blade (879).

Clamp pad (858) may be substantially similar to clamp pad (58a, 58b, 146) described above. By way of example only, clamp pad (858) may comprise a high temperature compatible, low wear, low friction material including polymers, elastomers, metals and ceramics or coated or filled versions thereof such as polytetrafluoroethylene, graphite-filled polytetrafluoroethylene, polyimide, fluorinated ethylene propylene, silicone, and/or any other suitable material (or combination of materials) as will be apparent to those of ordinary skill in the art in view of the teachings herein. By way of further example only, clamp pad (858) may further include fillers such as polytetrafluoroethylene, carbon, molybdenum disulfide, glass, metals (stainless, bronze, etc.), or calcium fluoride. By way of further example only, clamp pad (858) may further include one or more coatings such as FEP- or PTFE-based coatings. By way of further example only, clamp pad (858) may further comprise one or more ceramics such as alumina, zirconia, carbides, or nitrides. By way of further example only, clamp pad (858) may further comprise one or more polymers such as polyaryletherketone (PAEK) family of thermoplastics including PEEK, PEK, PEKK, PEEKK, PEKEKK and blends with other polymers such as PBI or fillers such as PTFE, graphite, carbon, molybdenum disulfide; polyimide and polyimide with fillers such as PTFE, graphite, carbon, molybdenum disulfide; PBI and PBI blended with other polymers; PTFE and PTFE with fillers such as graphite, carbon, molybdenum disulfide, glass, metalics (stainless, bronze, etc.), calcium fluoride; PPS; Polybenzimidazole-Polyetherketoneketone (PBI-PEKK); perfluoroalkoxy (PFA); glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos NanoTool. By way of further example only, clamp pad (858) may further include one or more elastomers such as silicones. Still other suitable materials that may be used to form clamp pad (858) will be apparent to those of ordinary skill in the art in view of the teachings herein.

Figure 20A:
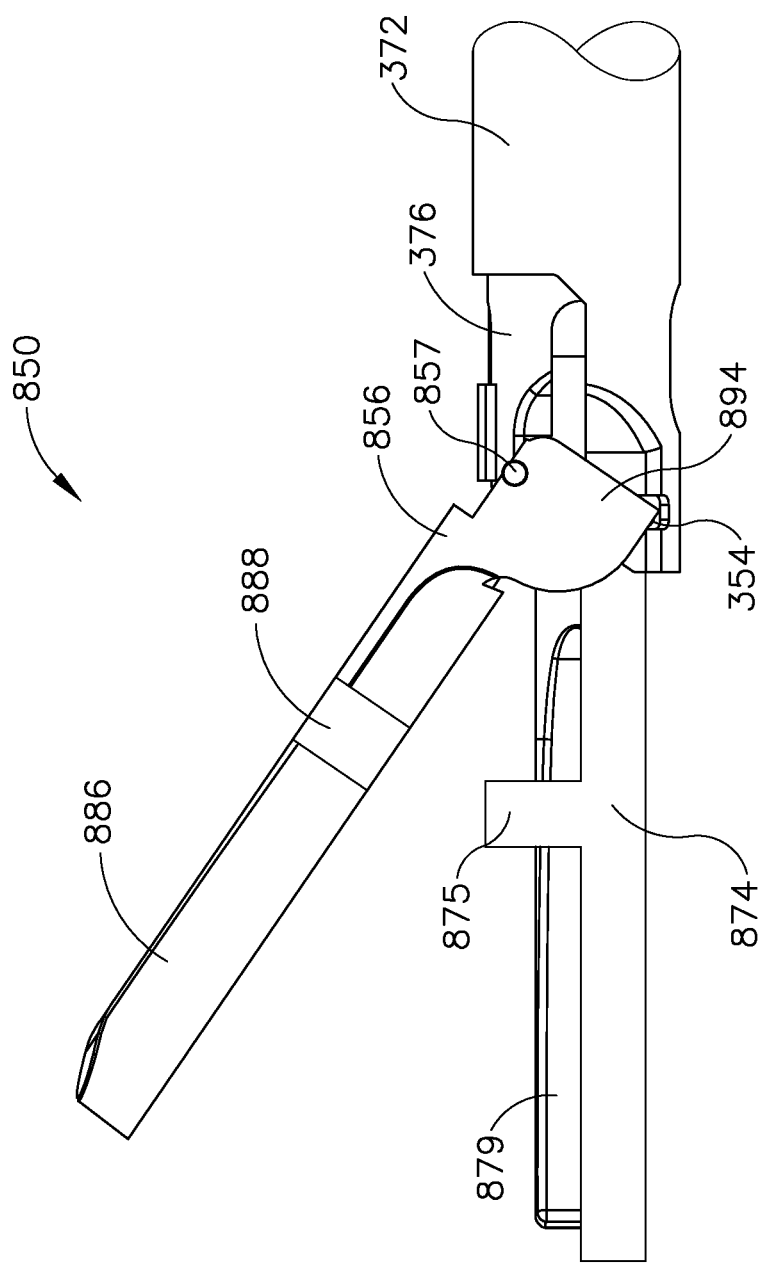
FIG. 20A depicts a side elevational view of another exemplary end effector that may be incorporated into the instrument of FIG. 2, with the end effector in an open configuration.
Figure 20B:
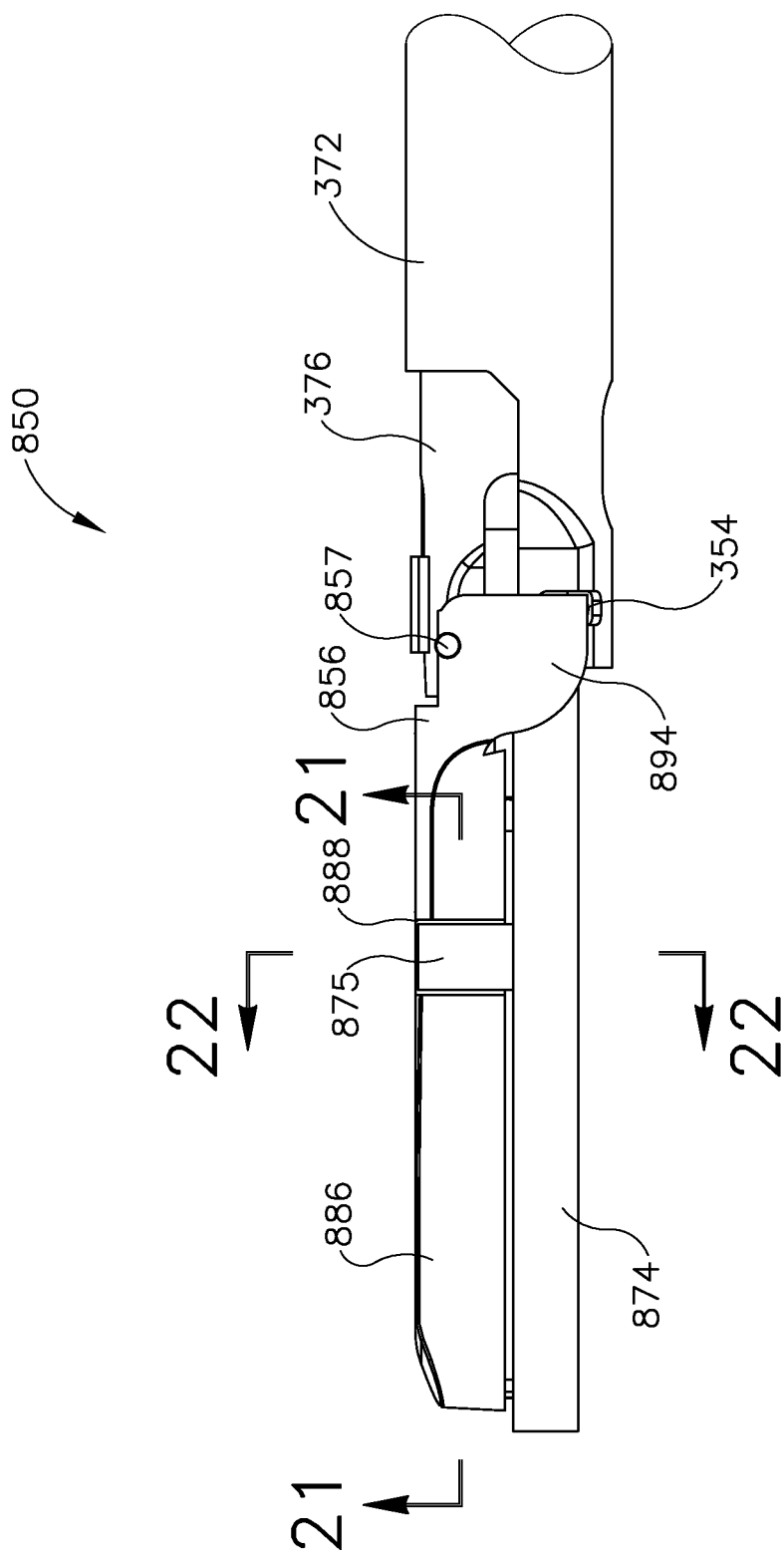
FIG. 20B depicts a side elevational view of the end effector of FIG. 20A, with the end effector in a closed configuration.
Figure 21:
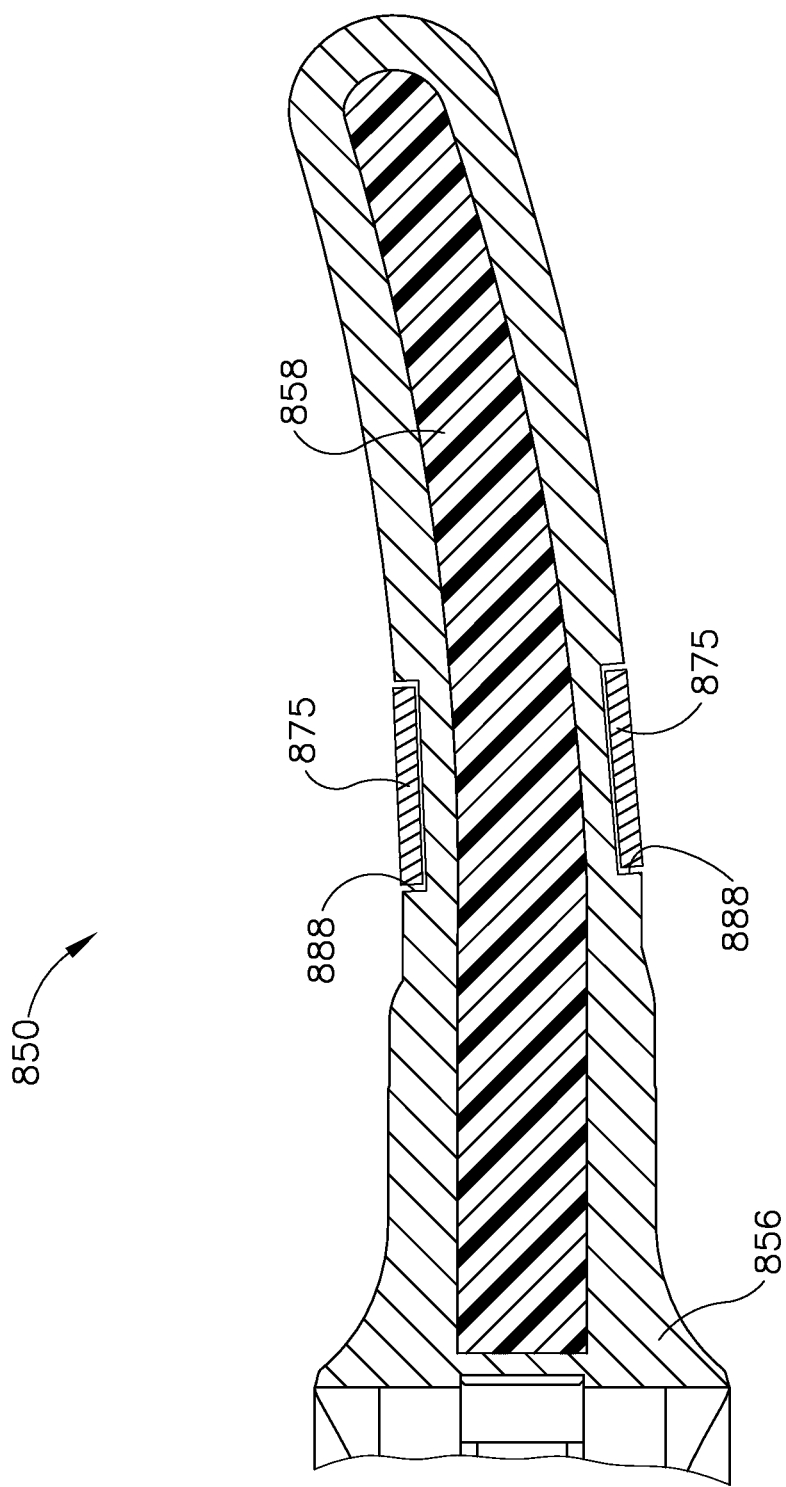
FIG. 21 depicts a cross-sectional view of the end effector of FIG. 20A taken line 21-21 of FIG. 20B.
Figure 22:
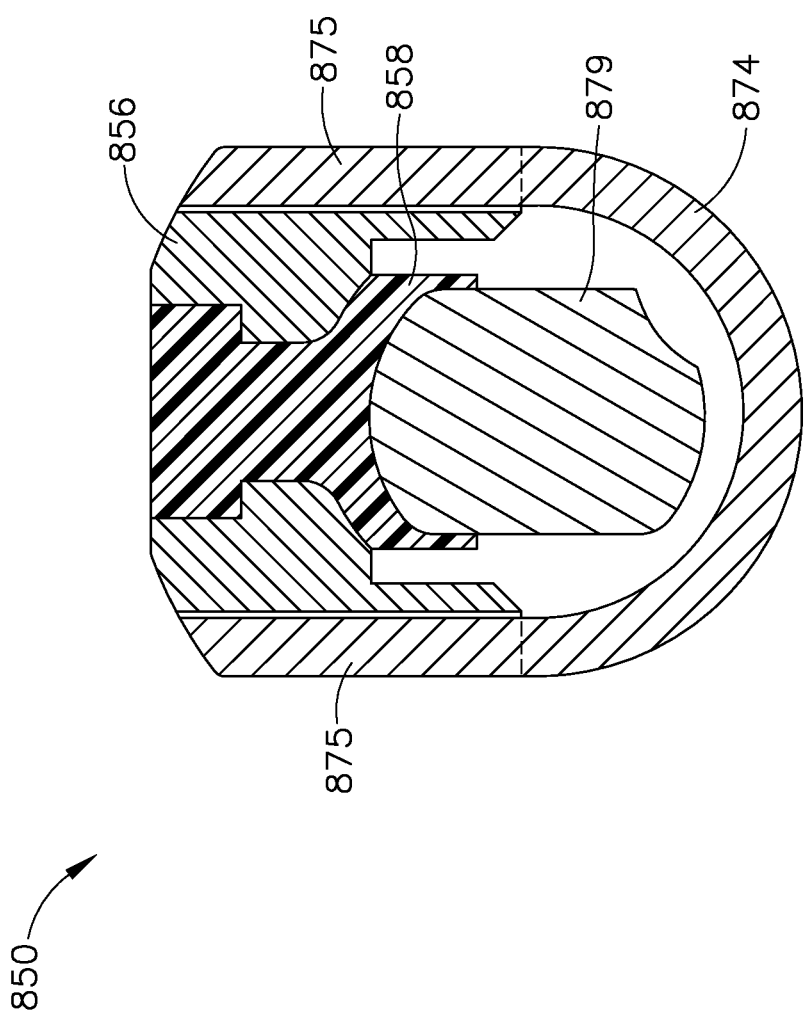
FIG. 22 depicts a cross-sectional view of the end effector of FIG. 20A taken along line 22-22 of FIG. 20B.

Clamp arm (856) includes a distal arm member (886), a pair of recesses (888), and a pair of support members (894). Similar to clamp arm (356), clamp arm (856) is coupled to opening (354) of outer sheath (372) and pivotally coupled to inner tube (376) via pivot pin (857). Therefore, translation of inner tube (376) relative to outer sheath (372) may pivot clamp arm (856) relative to blade (879) from an open position, as shown in FIG. 20A, to a closed position, as shown in FIG. 20B. Recesses (888) are dimensioned to receive protrusions (875) of extended blade sleeve (874) when clamp arm (856) rotates to a closed position. As best seen in FIG. 21, recesses (888) mate with protrusions (875) in such a way that protrusions (875) laterally align clamp arm (856) relative to blade (879). Additionally, as best seen in FIG. 22, because extended blade sleeve (874) is mechanically fixed in relation to ultrasonic blade (879), interaction between recesses (888) and protrusions (875) prevents clamp arm (856) from further lateral movement.

Contact between protrusions (875) of extended blade sleeve (874) and recesses (888) of clamp arm (856) may prevent clamp arm (856) from laterally deflecting relative to the longitudinal axis of blade (879). In other words, lateral positioning between clamp arm (856) and blade (879) may be more consistent due to contact between protrusions (875) and recesses (888), even in response to external forces imparted on end effector (850). This may allow for a narrower clamp arm (856) and/or clamp pad (858), as alignment between clamp pad (858) and clamp arm (856) may be more consistent. Additionally, contact between protrusions (875) of extended blade sleeve (874) and recesses (888) of clamp arm (856) may prevent clamp arm (856) from rotating about the longitudinal axis of blade (879). This may result in a more consistent distribution of forces imparted on tissue grasped by end effector (850). While the current example shows two protrusions (875) in contact with recesses (888), one protrusion (875) may be utilized with one slot (888).

In addition to ensuring alignment in end effector (850), protrusions (875) may also provide a positive tissue stop that may prevent tissue from traveling to a proximal region of end effector (850) where ultrasonic energy from blade (879) may not adequately sever or seal the tissue. In other words, protrusion (889) may prevent the tissue from reach in a longitudinal region of blade that is too close to a node associated with resonant ultrasonic vibrations communicated through blade (879). Such a positive tissue stop may thus consistently and simply prevent tissue from inadvertently reaching a proximal position within end effector (850) where the tissue would be undesirably unaffected by blade (879). In providing such prevention, the positive tissue stop may eliminate the need for an operator to visualize proximal region of end effector (850) in order to determine whether the tissue has reached an undesirably proximal position within end effector (850).

Figure 23A:
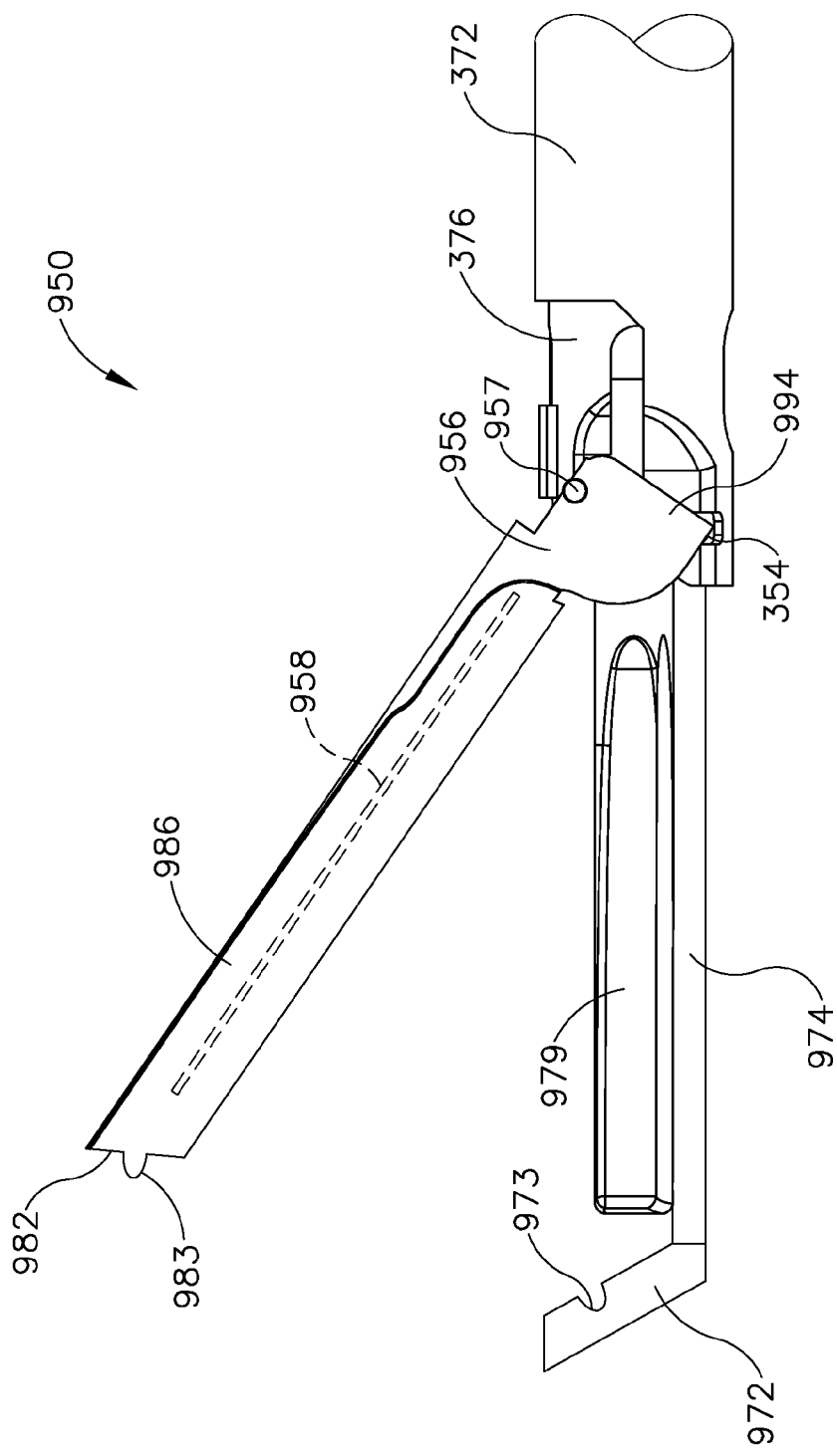
FIG. 23A depicts side elevational view of another exemplary end effector that may be incorporated into the instrument of FIG. 2, with the end effector in an open configuration.
Figure 23B:
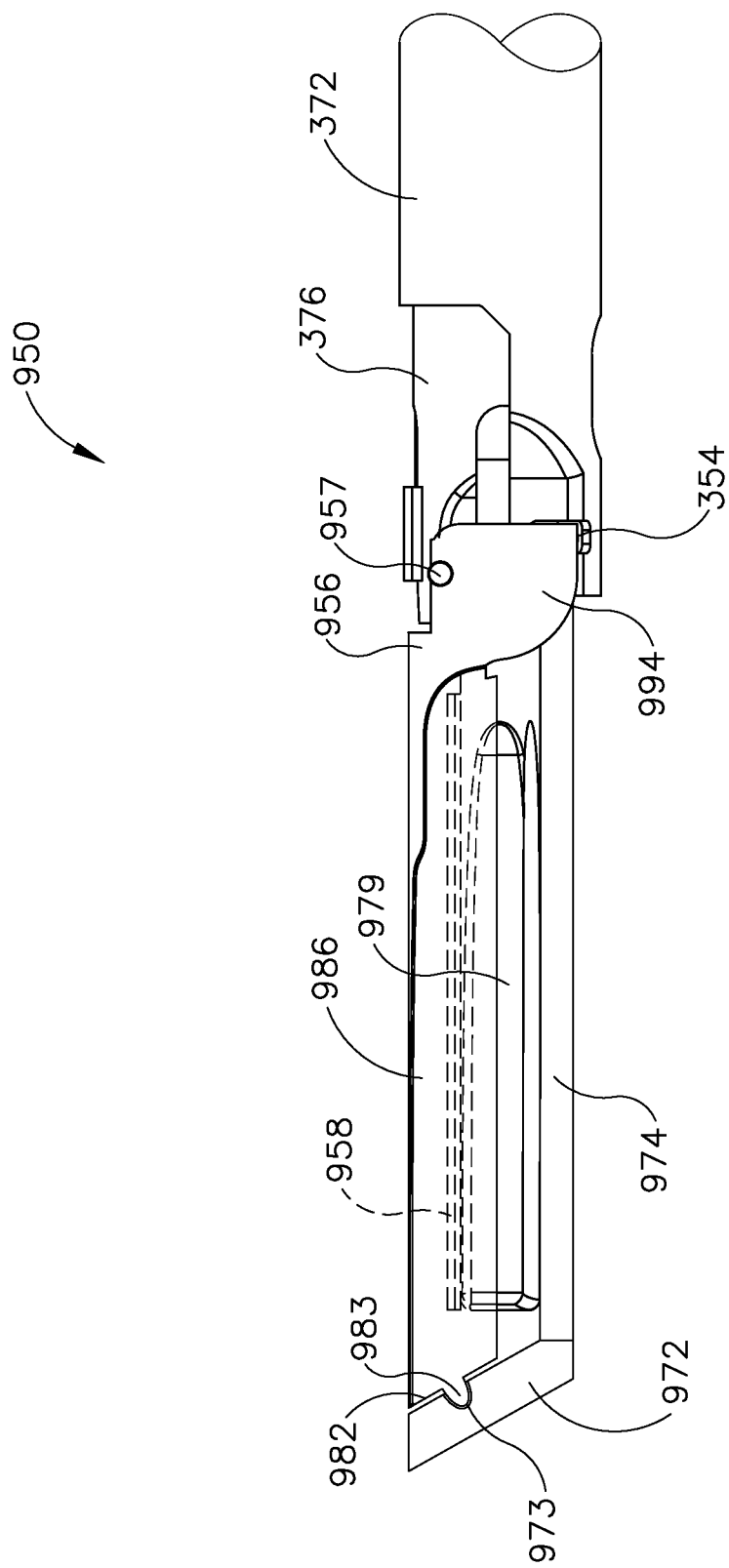
FIG. 23B depicts a side elevational view of the end effector of FIG. 23A, with the end effector in a closed configuration.

FIGS. 23A-23B show another exemplary end effector (950) attached to outer sheath (372) and inner tube (376). End effector (950), outer sheath (372) and inner tube (376) may be readily incorporated into instrument (20, 100, 200) described above. Therefore it should be understood that inner tube (376) is slidably disposed within outer sheath (372) Inner tube (376) is thus operable to translate longitudinally within outer sheath (372) relative to outer sheath (372) to selectively open and close end effector (950). Any of the methods described above used to slide inner tube (376) relative to outer sheath (372) may be utilized.

End effector (950) includes a clamp arm (956), a clamp pad (958) housed within clamp arm (956), an ultrasonic blade (979), and an extended blade sleeve (974) partially housing ultrasonic blade (979). Similar to end effector (850) as shown in FIG. 22, it should be understood that clamp pad (958) is positioned on clamp arm (956) such that clamp pad (958) faces blade (979) when end effector (950) is in a closed position. Clamp pad (958) may be substantially similar to clamp pad (58a, 58b, 146) described above.

By way of example only, clamp pad (958) may comprise a high temperature compatible, low wear, low friction material including polymers, elastomers, metals and ceramics or coated or filled versions thereof such as polytetrafluoroethylene, graphite-filled polytetrafluoroethylene, polyimide, fluorinated ethylene propylene, silicone, and/or any other suitable material (or combination of materials) as will be apparent to those of ordinary skill in the art in view of the teachings herein. By way of further example only, clamp pad (958) may further include fillers such as polytetrafluoroethylene, carbon, molybdenum disulfide, glass, metals (stainless, bronze, etc.), or calcium fluoride. By way of further example only, clamp pad (958) may further include one or more coatings such as FEP- or PTFE-based coatings. By way of further example only, clamp pad (958) may further comprise one or more ceramics such as alumina, zirconia, carbides, or nitrides. By way of further example only, clamp pad (958) may further comprise one or more polymers such as polyaryletherketone (PAEK) family of thermoplastics including PEEK, PEK, PEKK, PEEKK, PEKEKK and blends with other polymers such as PBI or fillers such as PTFE, graphite, carbon, molybdenum disulfide; polyimide and polyimide with fillers such as PTFE, graphite, carbon, molybdenum disulfide; PBI and PBI blended with other polymers; PTFE and PTFE with fillers such as graphite, carbon, molybdenum disulfide, glass, metalics (stainless, bronze, etc.), calcium fluoride; PPS; Polybenzimidazole-Polyetherketoneketone (PBI-PEKK); perfluoroalkoxy (PFA); glass-filled PFA; Polyamide-imide (PAI), such as TORLON; Thermoplastic Polyimide (TPI), such as EXTEM; Polyetherimide (PEI), such as ULTEM; carbon-filled PEI; Polyetheretherketone (PEEK); glass-filled Polyaryletherketone (PAEK); DSM Somos ProtoTherm 12120; and/or DSM Somos NanoTool. By way of further example only, clamp pad (958) may further include one or more elastomers such as silicones. Still other suitable materials that may be used to form clamp pad (958) will be apparent to those of ordinary skill in the art in view of the teachings herein.

It should be understood that extended blade sleeve (974) is similar to blade sleeve (374) in the fact extended blade sleeve (974) is fixed relative to outer sheath (372) and extends within inner tube (376). Extended blade sleeve (974) is also fixed relative to ultrasonic blade (979). Extended blade sleeve (974) also includes an angled distal portion (972) having a recess (973). As will be described in greater detail below, recess (983) helps align clamp arm (956) with ultrasonic blade (997) when end effector (950) is in a closed position.

Clamp arm (956) includes a distal arm member (986), an angled distal face (982) having a distal protrusion (983), and a pair of support members (994). Similar to clamp arm (356), clamp arm (956) is coupled to opening (354) of outer sheath (372) and pivotally coupled to inner tube (376) via pivot pin (957). Therefore, translation of inner tube (376) relative to outer sheath (372) may pivot clamp arm (956) relative to blade (979) from an open position, as shown in FIG. 23A, to a closed position, as shown in FIG. 23B. Angled distal face (982) and angled distal portion (972) have complementary angles, such that when end effector (950) is in a closed position, angled distal portion (972) and angled distal face (983) are flush with one another. However, angles of angled distal portion (972) and angled distal face (983) may utilize other angles such that angled distal portion (972) and angled distal face (983) are flush with each other at a position other than when end effector (950) is in a closed position. Any such variations would be apparent to one having ordinary skill in the art in view of the teachings herein. Distal protrusion (983) and recess (973) are configured to mate with each other when angled distal portion (972) and angled distal face (983) are flush and aligned. When distal protrusion (983) and recess (973) mate, clamp arm (956) is effectively aligned with blade (979).

Similar to end effector (350), end effector (950) could be configured to deliver RF electrosurgical energy to a surgical site through bipolar operation. As such, clamp arm (956) may be associated with one pole while an opposite pole may be associated with blade (979). Clamp pad (958) may act as an insulative material. Angled distal face (982) may be configured to extend distally past blade (979) in order to act as an electrode and generate a seal-only tissue effect at the angled distal face (982).

Contact between distal protrusion (983) and recess (973) may prevent clamp arm (956) from laterally deflecting relative to the longitudinal axis of blade (979). In other words, lateral positioning between clamp arm (956) and blade (979) may be more consistent due to the mating of distal protrusion (983) and recess (973), even in response to external forces imparted on end effector (950). This may allow for a narrower clamp arm (956) and/or clamp pad (958), as alignment between clamp pad (958) and clamp arm (956) may be more consistent. Additionally, mating between distal protrusion (983) and recess (973) may prevent clamp arm (956) from rotating about the longitudinal axis of blade (979). This may result in a more consistent distribution of forces imparted on tissue grasped by end effector (950). While the current example shows one distal protrusion (983) and one recess (973) any number of bumps (983) and recesses (973) may be utilized. It should also be understood that, similar to extended blade sleeve (874), extended blade sleeve (974) of the present example does not contact any portion of blade (979).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) a shaft assembly having an acoustic waveguide configured to acoustically couple with an ultrasonic transducer; and (b) an end effector projecting from the shaft assembly, the end effector including: (i) an ultrasonic blade in acoustic communication with the acoustic waveguide, (ii) a clamp arm coupled with the shaft assembly and configured to selectively move relative to the ultrasonic blade from an open position toward a closed position, the clamp arm and the ultrasonic blade being configured to receive the tissue therebetween in the open position and selectively move from the open position and toward the ultrasonic blade until reaching the closed position for compressing the tissue against the ultrasonic blade, the clamp arm including an abutment configured to engage a portion of the shaft assembly in the closed position thereby inhibiting further movement of the clamp arm toward the ultrasonic blade, and (iii) a first clamp pad coupled with the clamp arm and positioned between the clamp arm and the ultrasonic blade, wherein the clamp arm is configured to maintain a gap between the first clamp pad and the ultrasonic blade in response to engagement between the abutment and the corresponding portion of the shaft assembly.

Example 2

The ultrasonic surgical instrument of Example 1, wherein the abutment further includes a second clamp pad configured to engage the portion of the shaft assembly when the clamp arm is in the closed position.

Example 3

The ultrasonic surgical instrument of any one or more of Examples 1 through 2, wherein the abutment is configured to engage the acoustic waveguide when the clamp arm is in the closed position.

Example 4

The ultrasonic surgical instrument of Example 3, wherein the acoustic waveguide is configured to resonate and thereby define a nodal position, wherein the abutment is configured to engage the acoustic waveguide at the nodal position.

Example 5

The ultrasonic surgical instrument of any one or more of Examples 1 through 4, wherein the clamp arm has a distal arm portion and a proximal arm portion, wherein the distal arm portion includes the first clamp pad, wherein the proximal arm portion includes the abutment.

Example 6

The ultrasonic surgical instrument of Example 5, wherein the clamp arm is pivotally coupled to the shaft assembly about a pivot axis, wherein the pivot axis is positioned between the distal and proximal arm portions of the clamp arm such that the first clamp pad is configured to pivot toward the ultrasonic blade as the abutment pivots toward the shaft assembly.

Example 7

The ultrasonic surgical instrument of Example 6, wherein the abutment is configured to engage the acoustic waveguide when the clamp arm is in the closed position, and wherein the acoustic waveguide is configured to resonate and thereby define a nodal position, wherein the abutment is configured to engage the acoustic waveguide at the nodal position.

Example 8

The ultrasonic surgical instrument of any one or more of Examples 6 through 7, wherein the first clamp pad is configured to pivot downwardly toward the ultrasonic blade as the abutment simultaneously pivots upwardly toward the shaft assembly.

Example 9

The ultrasonic surgical instrument of any one or more of Examples 5 through 8, wherein the proximal arm portion further includes a first support member projecting proximally from the pivot axis, wherein the abutment extends from the first support member for engaging the portion of the shaft assembly.

Example 10

The ultrasonic surgical instrument of Example 9, wherein the proximal arm portion further includes a second support member projecting proximally from the pivot axis, wherein second support member is laterally offset from the first support member, wherein the abutment extends laterally between the first and second support members.

Example 11

The ultrasonic surgical instrument of any one or more of Examples 1 through 10, further comprising an actuator coupled to the clamp arm, wherein the actuator is configured to selectively direct movement of the clamp arm from the open position toward the closed position.

Example 12

The ultrasonic surgical instrument of Example 11, wherein the actuator includes a push-pull cable assembly coupled to the clamp arm to selectively direct movement of the clamp arm from the open position toward the closed position.

Example 13

The ultrasonic surgical instrument of Example 12, wherein the shaft assembly further comprises an inner tube configured to longitudinally translate relative to the waveguide, wherein the push-pull cable is connected to a distal end of the inner tube, the instrument further comprising a handle assembly having a trigger operatively connected to a proximal end of the inner tube, wherein the shaft assembly distally projects from the handle assembly, wherein the trigger is configured to selectively actuate the clamp arm via the push-pull cable.

Example 14

The ultrasonic surgical instrument of any one or more of Examples 1 through 13, further comprising a handle assembly configured to receive the ultrasonic transducer, wherein the shaft assembly distally projects from the handle assembly.

Example 15

The ultrasonic surgical instrument of Example 14, further comprising an ultrasonic transducer received within the handle assembly, wherein the ultrasonic transducer is operatively connected to the acoustic waveguide and configured to selectively oscillate the acoustic waveguide.

Example 16

An ultrasonic surgical instrument, comprising: (a) a shaft assembly having an acoustic waveguide configured to acoustically couple with an ultrasonic transducer; and (b) an end effector projecting from the shaft assembly, the end effector including: (i) an ultrasonic blade in acoustic communication with the acoustic waveguide, (ii) a clamp arm coupled with the shaft assembly and configured to selectively move relative to the ultrasonic blade from an open position toward a closed position, the clamp arm and the ultrasonic blade being configured to receive the tissue therebetween in the open position and selectively move from the open position and toward the ultrasonic blade until reaching the closed position for compressing the tissue against the ultrasonic blade, and (iii) a first clamp pad coupled with the clamp arm and positioned between the clamp arm and the ultrasonic blade, wherein the clamp arm is configured to prevent direct contact between the first clamp pad and the ultrasonic blade when the clamp arm is in the closed position.

Example 17

The ultrasonic surgical instrument of Example 16, further comprising: (a) a handle assembly, wherein the shaft projects distally from the handle assembly, and (b) an actuator operatively connected to the clamp arm and the handle assembly, wherein the actuator is configured to selectively direct movement of the clamp arm from the open position toward the closed position, wherein at least one of the clamp arm, the actuator, and the handle assembly includes an abutment configured to inhibit further movement beyond the closed position and toward the ultrasonic blade to thereby establish a minimum gap between the first clamp pad and the ultrasonic blade.

Example 18

An ultrasonic surgical instrument, comprising: (a) a shaft assembly having an acoustic waveguide configured to acoustically couple with an ultrasonic transducer; and (b) an end effector projecting distally from the shaft assembly, the end effector comprising: (i) an ultrasonic blade in acoustic communication with the acoustic waveguide, (ii) a clamp arm coupled with the shaft assembly at a pair of pivots, wherein the clamp arm is configured to selectively move relative to the ultrasonic blade from an open position toward a closed position, wherein the clamp arm and the ultrasonic blade are configured to receive the tissue therebetween in the open position, wherein the clamp arm is configured to compress tissue against the ultrasonic blade in the closed position, and (iii) an alignment feature located distal to the pair of pivots, wherein the alignment feature is configured to provide one or both of lateral alignment or rotational alignment between the clamp arm and the ultrasonic blade as the clamp arm moves toward the closed position, wherein the alignment feature is further configured to restrict proximal passage of tissue between the clamp arm and the ultrasonic blade.

Example 19

The ultrasonic surgical instrument of Example 18, wherein the clamp arm further comprises a laterally presented recess, wherein the end effector further comprises a blade sleeve, wherein the alignment feature extends from the blade sleeve toward the clamp arm, wherein the recess is configured to receive the alignment feature to provide lateral alignment between the clamp arm and the ultrasonic blade as the clamp arm moves toward the closed position.

Example 20

The ultrasonic surgical instrument of claim 18, wherein the alignment feature comprises a projection extending from the clamp arm toward the ultrasonic blade, wherein the projection is configured to engage a laterally presented surface of the ultrasonic blade to provide lateral alignment between the clamp arm and the ultrasonic blade as the clamp arm moves toward the closed position.

VII. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
    (a) a shaft assembly having an acoustic waveguide configured to acoustically couple with an ultrasonic transducer; and
    (b) an end effector projecting from the shaft assembly, the end effector including:
        (i) an ultrasonic blade in acoustic communication with the acoustic waveguide,
        (ii) a clamp arm coupled with the shaft assembly and configured to selectively move relative to the ultrasonic blade from an open position toward a closed position, the clamp arm and the ultrasonic blade being configured to receive the tissue therebetween in the open position and selectively move from the open position and toward the ultrasonic blade until reaching the closed position for compressing the tissue against the ultrasonic blade, the clamp arm including an abutment configured to engage a portion of the shaft assembly in the closed position thereby inhibiting further movement of the clamp arm toward the ultrasonic blade, and (iii) a first clamp pad coupled with the clamp arm and positioned between the clamp arm and the ultrasonic blade, wherein the clamp arm is configured to maintain a gap between the first clamp pad and the ultrasonic blade in response to engagement between the abutment and the corresponding portion of the shaft assembly.

2. The ultrasonic surgical instrument of claim 1, wherein the abutment further includes a second clamp pad configured to engage the portion of the shaft assembly when the clamp arm is in the closed position.

3. The ultrasonic surgical instrument of claim 1, wherein the abutment is configured to engage the acoustic waveguide when the clamp arm is in the closed position.

4. The ultrasonic surgical instrument of claim 3, wherein the acoustic waveguide is configured to resonate and thereby define a nodal position, wherein the abutment is configured to engage the acoustic waveguide at the nodal position.

5. The ultrasonic surgical instrument of claim 1, wherein the clamp arm has a distal arm portion and a proximal arm portion, wherein the distal arm portion includes the first clamp pad, wherein the proximal arm portion includes the abutment.

6. The ultrasonic surgical instrument of claim 5, wherein the clamp arm is pivotally coupled to the shaft assembly about a pivot axis, wherein the pivot axis is positioned between the distal and proximal arm portions of the clamp arm such that the first clamp pad is configured to pivot toward the ultrasonic blade as the abutment pivots toward the shaft assembly.

7. The ultrasonic surgical instrument of claim 6, wherein the abutment is configured to engage the acoustic waveguide when the clamp arm is in the closed position, and wherein the acoustic waveguide is configured to resonate and thereby define a nodal position, wherein the abutment is configured to engage the acoustic waveguide at the nodal position.

8. The ultrasonic surgical instrument of claim 6, wherein the first clamp pad is configured to pivot downwardly toward the ultrasonic blade as the abutment simultaneously pivots upwardly toward the shaft assembly.

9. The ultrasonic surgical instrument of claim 5, wherein the proximal arm portion further includes a first support member projecting proximally from the pivot axis, wherein the abutment extends from the first support member for engaging the portion of the shaft assembly.

10. The ultrasonic surgical instrument of claim 9, wherein the proximal arm portion further includes a second support member projecting proximally from the pivot axis, wherein second support member is laterally offset from the first support member, wherein the abutment extends laterally between the first and second support members.

11. The ultrasonic surgical instrument of claim 1, further comprising an actuator coupled to the clamp arm, wherein the actuator is configured to selectively direct movement of the clamp arm from the open position toward the closed position.

12. The ultrasonic surgical instrument of claim 11, wherein the actuator includes a push-pull cable assembly coupled to the clamp arm to selectively direct movement of the clamp arm from the open position toward the closed position.

13. The ultrasonic surgical instrument of claim 12, wherein the shaft assembly further comprises an inner tube configured to longitudinally translate relative to the waveguide, wherein the push-pull cable is connected to a distal end of the inner tube, the instrument further comprising a handle assembly having a trigger operatively connected to a proximal end of the inner tube, wherein the shaft assembly distally projects from the handle assembly, wherein the trigger is configured to selectively actuate the clamp arm via the push-pull cable.

14. The ultrasonic surgical instrument of claim 1, further comprising a handle assembly configured to receive the ultrasonic transducer, wherein the shaft assembly distally projects from the handle assembly.

15. The ultrasonic surgical instrument of claim 14, further comprising an ultrasonic transducer received within the handle assembly, wherein the ultrasonic transducer is operatively connected to the acoustic waveguide and configured to selectively oscillate the acoustic waveguide.

16. An ultrasonic surgical instrument, comprising:
(a) a shaft assembly having an acoustic waveguide configured to acoustically couple with an ultrasonic transducer; and
(b) an end effector projecting from the shaft assembly, the end effector including:
  (i) an ultrasonic blade in acoustic communication with the acoustic waveguide,
  (ii) a clamp arm coupled with the shaft assembly and configured to selectively move relative to the ultrasonic blade from an open position toward a closed position, the clamp arm and the ultrasonic blade being configured to receive the tissue therebetween in the open position and selectively move from the open position and toward the ultrasonic blade until reaching the closed position for compressing the tissue against the ultrasonic blade, and
  (iii) a first clamp pad coupled with the clamp arm and positioned between the clamp arm and the ultrasonic blade,
  wherein the clamp arm is configured to prevent direct contact between the first clamp pad and the ultrasonic blade when the clamp arm is in the closed position.

17. The ultrasonic surgical instrument of claim 16, further comprising:
(a) a handle assembly, wherein the shaft projects distally from the handle assembly, and
(b) an actuator operatively connected to the clamp arm and the handle assembly, wherein the actuator is configured to selectively direct movement of the clamp arm from the open position toward the closed position,
wherein at least one of the clamp arm, the actuator, and the handle assembly includes an abutment configured to inhibit further movement beyond the closed position and toward the ultrasonic blade to thereby establish a minimum gap between the first clamp pad and the ultrasonic blade.

18. An ultrasonic surgical instrument, comprising:
(a) a shaft assembly having an acoustic waveguide configured to acoustically couple with an ultrasonic transducer; and
(b) an end effector projecting distally from the shaft assembly, the end effector comprising:
  (i) an ultrasonic blade in acoustic communication with the acoustic waveguide,
  (ii) a clamp arm coupled with the shaft assembly at a pair of pivots, wherein the clamp arm is configured to selectively move relative to the ultrasonic blade from an open position toward a closed position, wherein the clamp arm and the ultrasonic blade are configured to receive the tissue therebetween in the open position, wherein the clamp arm is configured to compress tissue against the ultrasonic blade in the closed position, and (iii) a blade sleeve secured relative to the ultrasonic blade and including an alignment feature located distal to the pair of pivots, wherein the alignment feature extends from the blade sleeve toward the clamp arm and is configured to provide one or both of lateral alignment or rotational alignment between the clamp arm and the ultrasonic blade as the clamp arm moves toward the closed position, wherein the alignment feature is further configured to restrict proximal passage of tissue between the clamp arm and the ultrasonic blade.

19. The ultrasonic surgical instrument of claim 18, wherein the clamp arm further comprises a laterally presented recess, wherein the recess is configured to receive the alignment feature to provide lateral alignment between the clamp arm and the ultrasonic blade as the clamp arm moves toward the closed position.

20. The ultrasonic surgical instrument of claim 18, wherein the alignment feature comprises a projection extending from the clamp arm toward the ultrasonic blade, wherein the projection is configured to engage a laterally presented surface of the ultrasonic blade to provide lateral alignment between the clamp arm and the ultrasonic blade as the clamp arm moves toward the closed position.

* * * * *